United States Patent [19]

Begley et al.

[11] Patent Number: 5,026,628

[45] Date of Patent: Jun. 25, 1991

[54] PHOTOGRAPHIC MATERIAL AND PROCESS COMPRISING A COMPOUND CAPABLE OF FORMING A WASH-OUT DYE

[75] Inventors: William J. Begley, Webster; Teh-Hsuan Chen, Fairport; Kenneth N. Kilminster, Rochester; Jerrold N. Poslusny, Rochester; Wojciech Slusarek, Rochester, all of N.Y.

[73] Assignee: Eastman Kodak Company, Rochester, N.Y.

[21] Appl. No.: 483,600

[22] Filed: Feb. 22, 1990

[51] Int. Cl.$^5$ .................. G03C 5/54; G03C 7/32; G03C 1/06; G03C 1/34

[52] U.S. Cl. .................. 430/382; 430/223; 430/226; 430/376; 430/434; 430/512; 430/543; 430/544; 430/549; 430/553; 430/555; 430/557; 430/558; 430/559; 430/564; 430/566; 430/598; 430/607; 430/611; 430/621; 430/955; 430/957; 430/959

[58] Field of Search .............. 430/955, 957, 959, 223, 430/226, 544, 549, 553, 555, 557, 558, 559, 551, 572, 564, 566, 598, 611, 607, 621, 376, 382, 443, 445, 434

[56] References Cited

U.S. PATENT DOCUMENTS

| | | | |
|---|---|---|---|
| 3,227,554 | 1/1966 | Barr et al. | 430/226 |
| 4,248,962 | 2/1981 | Lou | 430/382 |
| 4,409,323 | 10/1983 | Sato et al. | 430/544 |
| 4,482,629 | 11/1984 | Nakagawa et al. | 430/544 |
| 4,847,185 | 7/1989 | Begley et al. | 430/376 |
| 4,857,440 | 8/1989 | Begley et al. | 430/382 |
| 4,857,447 | 8/1989 | Tamoto et al. | 430/544 |
| 4,861,701 | 8/1989 | Burns et al. | 430/543 |

OTHER PUBLICATIONS

*Research Disclosure*, Dec. 1989, Item #308119, Kenneth Mason Publications, Hampshire, England.

Primary Examiner—Richard L. Schilling
Attorney, Agent, or Firm—Richard E. Knapp

[57] ABSTRACT

Photographic compound (A) capable of releasing a photographically useful group is represented by the formula: SOL-CAR-LINK-PUG wherein SOL is a water-solubilizing group; CAR is a carrier moiety that, upon reaction with oxidized developing agent, is capable of releasing LINK-PUG and capable of forming a compound that is washed out of the photographic element during photographic processing; LINK-PUG is in turn capable of releasing a photographically useful group (PUG) during photographic processing and LINK-PUG is represented by the formula:

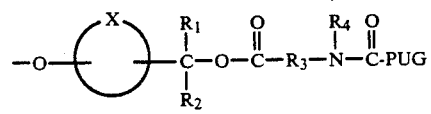

wherein X, $R_1$, $R_2$, $R_3$, $R_4$ and PUG are as defined in the application. The photographic compound (A) enables formation of easily removable compounds in photographic elements and processes that provide images having improved acutance.

12 Claims, No Drawings

PHOTOGRAPHIC MATERIAL AND PROCESS COMPRISING A COMPOUND CAPABLE OF FORMING A WASH-OUT DYE

This invention relates to a new photographic compound that is capable of forming a wash-out dye in a photographic material upon photographic processing to form an image having improved acutance and to a photographic material and process using such a compound.

Various ways are recognized in the photographic art for release of a photographically useful group (PUG) from a compound, such as a coupler, in a photographic material and process. For example, U.S. Pat. No. 4,248,962 describes compounds that release photographically useful groups by means of an intramolecular nucleophilic displacement reaction in photographic materials. Other examples of means for release of photographically useful groups are described in, for example, U.S. Pat. Nos. 4,409,323 and 4,861,701. These compounds, particularly couplers, capable of releasing a photographically useful group provide a degree of control over timing and rate of release as well as rate of diffusion and distance of diffusion of the photographically useful group.

The part of the compound that remains in the photographic material after release of the photographically useful group and the dye that is formed in the material from reaction with oxidized color developer often provides undesired properties in the photographic material during or after photographic processing. For example the dye formed from a coupler upon release of a photographically useful group often adversely affects the desired image. One answer to this has been to provide a coupler that has a water solubilizing group on the parent coupler to enable the dye formed from the coupler to be washed-out of the photographic element upon photographic processing. Such couplers are described, for example, in U.S. Pat. No. 4,482,629.

A need has existed to provide a compound, particularly a coupler, in a photographic material and process that enables formation of an image having improved acutance while enabling removal by wash-out of the dye formed from the compound, particularly the dye formed from the coupler during photographic processing. Moreover, such needs have existed with the added parameter that such a compound must not require significantly modifying the photographically useful groups in a way that would adversely affect the ultimate end use of the groups.

The present invention solves these problems by means of a photographic element comprising a support bearing at least one photographic silver halide emulsion layer and at least one compound (A) represented by the formula SOL-CAR-LINK-PUG wherein SOL is a water solubilizing group, CAR is a carrier moiety that, upon reaction with oxidized color developing agent, is capable of releasing LINK-PUG and capable of forming a compound that is washed out of the photographic element during photographic processing; wherein LINK-PUG is in turn capable of releasing a photographically useful group (PUG) during photographic processing; and, LINK-PUG is represented by the formula:

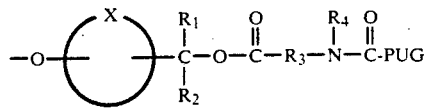

wherein

X represents the atoms necessary to complete an unsubstituted or substituted arylene, preferably unsubstituted or substituted phenylene or naphthylene, or heterocyclic group;

$R_1$ and $R_2$ individually are hydrogen or alkyl, preferably alkyl containing 1 to 40 carbon atoms or aryl, such as unsubstituted or substituted phenyl, or $R_1$ and $R_2$ together may complete a ring system, such as a 4-, 5- or 6-member ring;

$R_3$ is a divalent group that enables formation of a ring, particularly a 5-, 6- or 7-member ring, upon processing of the photographic element;

$R_4$ is hydrogen, unsubstituted or substituted alkyl, or unsubstituted or substituted aryl or may represent the atoms completing a ring with $R_3$, such as a 5- or 6-member ring; and, PUG is a releasable photographically useful group. CAR is preferably a coupler moiety, such as a cyan, magenta or yellow dye-forming coupler moiety.

Preferred LINK groups can contain a ballast on the ring completed by X or be part of $R_1$ or $R_2$ as described.

Preferred illustrative examples of LINK-PUG are represented by the formula:

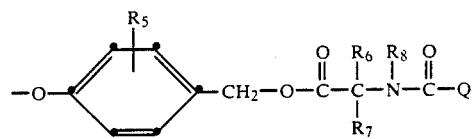

or

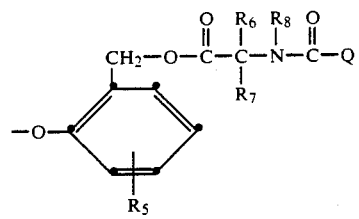

wherein $R_5$ is hydrogen or a substituent group, particularly a substituent group that does not adversely affect the desired properties of the desired image;

$R_6$ and $R_7$ individually are hydrogen, unsubstituted or substituted alkyl, such as alkyl containing 1 to 8 carbon atoms, or unsubstituted or substituted aryl, such as aryl containing 6 to 10 carbon atoms;

$R_8$ is alkyl, cycloalkyl, heterocyclyl or aryl; and

Q is a releasable photographically useful group, particularly a releasable development inhibitor group.

A preferred compound (A) is a dye-forming coupler of the form SOL-COUP-LINK-PUG in which COUP is a coupler moiety and SOL and LINK-PUG are as described.

A process of forming an image having the described advantages comprises developing an exposed photographic element by means of a color developing agent in the presence of described compound (A), particularly a coupler as described.

The water solubilizing group SOL can be any water solubilizing group known in the photographic art to enable wash-out of the dye formed in photographic processing from the compound (A). Typical water-solubilizing groups include groups terminated with an acid group, such as carboxy, sulfo or hydroxy which may also form a salt and other groups described in U.S. Pat. No. 4,482,629 (col. 4, lines 1–3). The compound (A) can have one or more water-solubilizing groups. The number and type of water solubilizing groups should not be sufficient to make the compound (A) mobile in the photographic element prior to exposure and processing. The LINK-PUG can also contain one or more water-solubilizing groups if desired.

A typical water-solubilizing group SOL is a carbonamido group —CONHR$_a$ wherein R$_a$ is an alkyl group containing 1 to 3 carbon atoms, preferably —CONHCH$_3$ or —CONHC$_2$H$_5$; or a group containing a water-solubilizing group, such as carboxy, sulfo or hydroxy groups, for instance, —CONH$_2$CH$_2$CH$_2$OH, —CONH$_2$CH$_2$CO$_2$H, or —CONH$_2$CH$_2$CH$_2$CO$_2$H. Such a group can be, for example, in the 2-position of a naphtholic coupler containing LINK-PUG in the coupling position.

During photographic processing, the reaction of compound (A), preferably a coupler, with oxidized color developing agent cleaves the bond between the coupling-off group (LINK-PUG) and the carrier portion of the compound (A), preferably the coupler moiety (COUP). Then the bond between the first part of the LINK and the second part of the LINK is cleaved. The first part of the LINK includes the aryloxy or heterooxy group that contains the group containing the carbon atom containing R$_1$ and R$_2$. This first part of the LINK is, for example, as described in U.S. Pat. No. 4,409,323. The bond between the second part of the LINK and the PUG is then cleaved. The cleavage of the bond between the PUG and the second part of the LINK is enabled by an intramolecular nucleophilic displacement reaction. Tailoring of the particular parts of the LINK to requirements of the given PUG allows control over the timing and rate of release of the PUG.

The divalent groups for R$_3$ can be any group that provides proper distance between the specified carboxyl group and the nitrogen atom to allow intramolecular nucleophilic displacement to occur with suitable timing of release of the PUG. Such groups include, for example, unsubstituted or substituted alkylene, arylene groups, spiro ring systems and heterocyclic ring systems.

Particularly useful compounds as described are couplers as represented by the formula:

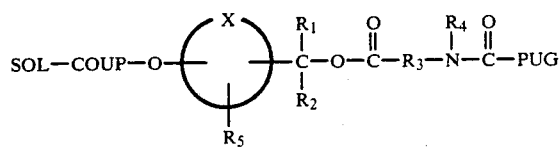

wherein

SOL is a water-solubilizing group, as described, preferably —COOH or —CONHCH$_3$;

COUP is a dye-forming coupler, such as a cyan, magenta or yellow dye-forming coupler, having the remainder of the molecule substituted in the coupling position;

X represents the atoms necessary to complete an unsubstituted or substituted arylene, preferably phenylene, or heterocyclic group;

R$_1$ and R$_2$ individually represent hydrogen or alkyl, such as alkyl containing 1 to 40 carbon atoms;

R$_3$ is a divalent group that enables formation of a ring, particularly a 5-, 6- or 7-member ring, upon processing the photographic element;

R$_4$ is hydrogen, unsubstituted or substituted alkyl or unsubstituted or substituted aryl;

R$_5$ is hydrogen or a substituent, as described, such as unsubstituted or substituted alkyl or aryl, or a sulfonamido group, preferably a ballast group; and, PUG is a releasable photographically useful group, preferably a releasable development inhibitor group. When the PUG is a releasable development inhibitor group improved image acutance and improved interimage effects are observed in a photographic element of the invention.

An especially useful compound (A), preferably a coupler, comprises a LINK-PUG represented by the formula:

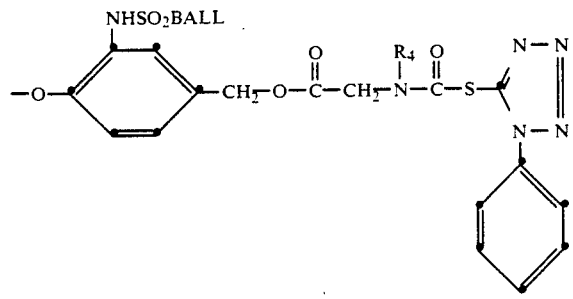

wherein BALL is a ballast group and R$_4$ is as described, preferably a phenyl group.

As used herein BALL is a ballast group that is known in the photographic art. The ballast group as described is an organic group of such size and configuration as to confer on the molecule sufficient bulk to render the molecule substantially non-diffusible from the layer in which it is coated in a photographic element. Representative ballast groups include substituted or unsubstituted alkyl or aryl groups typically containing 8 to 40 carbon atoms.

The group R$_4$ is typically an electron density controlling group containing an electron withdrawing group or electron donating group.

A preferred compound (A) is a dye-forming coupler of the form COUP-LINK-PUG in which COUP is a coupler moiety and LINK-PUG is a coupling-off group.

A process of forming an image having the described advantages comprises developing an exposed photographic element by means of a color developing agent in the presence of described compound (A), particularly a coupler as described.

The compound (A), preferably a coupler, contains a coupling-off group -LINK-PUG that enables increased resistance to hydrolysis during storage. It also enables increased acutance of an image formed upon processing a photographic silver halide element containing the compound (A) when PUG is a development inhibitor moiety.

Illustrative preferred groups that are bonded to the

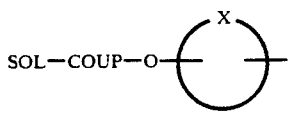

portion of the compound (A) are represented by the formulas:

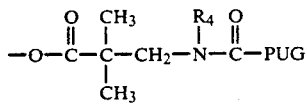

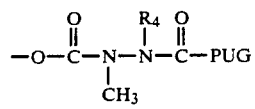

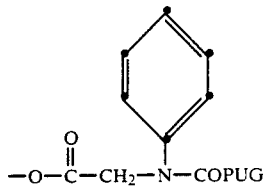

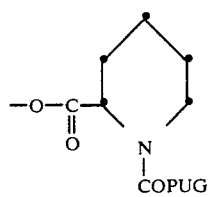

and

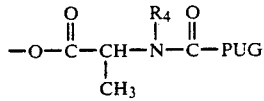

wherein R₄ is as described, especially an electron density controlling group comprising an electron withdrawing group or an electron donating group as known in the organic compound synthesis art, such as an aryl group or alkyl group. These improvements for compounds of the invention are demonstrated by the data in the photographic examples when compared to couplers of the type described in U.S. Pat. No. 4,248,962.

The reaction of compound (A), preferably a development inhibitor releasing (DIR) coupler, with oxidized color developing agent cleaves the bond between the coupling-off group and the carrier portion of the compound (A), preferably the coupler moiety (COUP). Then the bond between the photographically useful group and the remainder of the coupling-off group is cleaved. Bond cleavage between the PUG and the remainder of the coupling-off group preferably does not involve the action of oxidized color developing agent. The cleavage of the bond between the PUG and the remainder of the coupling-off group is enabled by an intramolecular nucleophilic displacement reaction. Tailoring the structure of the LINK moiety to the requirements of a given PUG allows control over timing and rate of release of the PUG. The sequential cleavage of the bond between the coupling-off group and the carrier portion of the compound A and the bond between the PUG and the remainder of the coupling-off group is a characteristic feature of the compounds as described.

Particularly useful compounds as described are couplers represented by the formula:

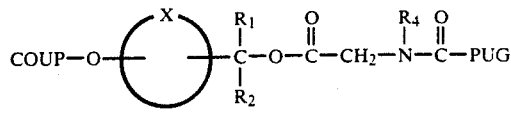

wherein COUP, X, R₁, R₂, R₄ and PUG are as described.

Examples of useful electron withdrawing groups as described for R₄ include:

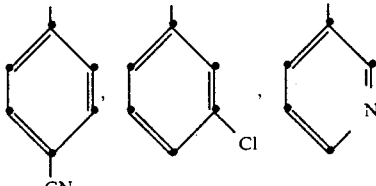

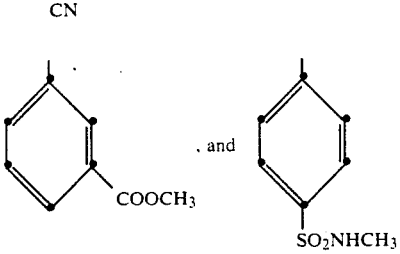

Examples of useful electron donating groups as described for R₄ include:

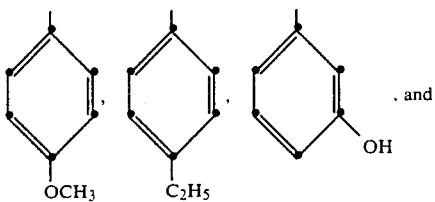

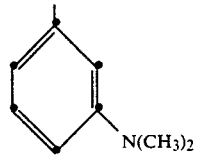

When PUG is a development inhibitor, for instance, useful release times are generally achieved when R₄ is an aryl group if PUG is a mercaptotetrazole derivative.

As used herein the terms "coupler" and "coupler compound" refer to the entire compound, including the coupler moiety and the coupling-off group including the PUG. The term "coupler moiety" refers to that portion of the compound other than the coupling-off group.

The coupler moiety (COUP) can be any moiety that will react with oxidized color developing agent to cleave the bond between the LINK portion of the coupling-off group and the coupler moiety. The coupler moiety herein includes coupler moieties employed in conventional color-forming couplers that yield colorless products on reaction with oxidized color developing agents as well as coupler moieties that yield colored products on reaction with oxidized color developing agents. Both types of coupler moieties are well known to those skilled in the photographic art.

The coupler moiety can be ballasted or unballasted provided that the dye formed upon oxidative coupling is capable of being washed out of the photographic element. It can be monomeric, or it can be part of a dimeric, oligomeric or polymeric coupler, in which case more than one group containing PUG can be contained in the coupler, or it can form part of a bis compound in which the PUG forms part of a link between two coupler moieties.

As used herein, the term "intramolecular nucleophilic displacement reaction" means a reaction in which a nucleophilic center of a compound reacts directly, or indirectly through an intervening molecule, at another site on the compound, that is an electrophilic center, to effect displacement of a group or atom attached to the electrophilic center. Such compounds have a nucleophilic group and electrophilic group spacially related by the configuration of the molecule to promote reactive proximity. The electrophilic group and the nucleophilic group are located in the coupling-off group as described so that a cyclic organic ring, or a transient cyclic organic ring can be easily formed by an intramolecular reaction involving the nucleophilic center and the electrophilic center.

A nucleophilic group is understood to be a grouping of atoms one of which is electron rich. This atom is referred to as the nucleophilic center. An electrophilic group is understood to be a grouping of atoms one of which is electron deficient. This is referred to as the electrophilic center.

The PUG can be any group that is typically made available in a photographic element in an imagewise fashion. The PUG can be a photographic reagent or a photographic dye. A photographic reagent herein is a moiety that upon release further reacts with components in the photographic element, such as a development inhibitor, a development accelerator, a bleach inhibitor, a bleach accelerator, a coupler (for example, a competing coupler, a dye-forming coupler, or a development inhibitor releasing coupler (DIR coupler)), a dye precursor, a dye, a developing agent (for example, a competing developing agent, a dye-forming developing agent, or a silver halide developing agent), a silver complexing agent, a fixing agent, an image toner, a stabilizer, a hardener, a tanning agent, a fogging agent, an ultraviolet radiation absorber, an antifoggant, a nucleator, a chemical or spectral sensitizer or a desensitizer.

The PUG can be present in the coupling-off group as a preformed species or it can be present in a blocked form or as a precursor. The PUG can be for example a preformed development inhibitor or the development inhibiting function can be blocked by being the point of attachment to the carbonyl group bonded to PUG in the coupling-off group. Other examples are a preformed dye, a dye that is blocked to shift its absorption, and a leuco dye.

There follows a listing of patents and publications that describe representative COUP groups useful in the invention:

COUP's

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturübersicht," published in Agfa Mitteilungen, Band III, pp. 156–175 (1961).

Preferably such couplers are phenols and naphthols which form cyan dyes on reaction with oxidized color developing agent.

B. Couplers which form magenta dyes upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturübersicht," published in Agfa Mitteilungen, Band III, pp. 126–156 (1961).

Preferably such magenta dye-forming couplers are pyrazolones or pyrazolotriazole couplers.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Literaturü bersicht," published in Agfa Mitteilungen, Band III, pp. 112–126 (1961).

Preferably such yellow dye-forming couplers are acylacetamides, such as benzoylacetamides and pivaloylacetamides.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959.

PUG groups that are useful include, for example:

PUG's

A. PUG's which form development inhibitors upon release are described in such representative patents as U.S. Pat. Nos. 3,227,554; 3,384,657; 3,615,506; 3,617,291; 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, oxadiazoles, benzotriazoles and benzodiazoles. Structures of preferred development inhibitor moieties are:

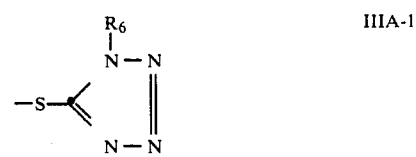

IIIA-1

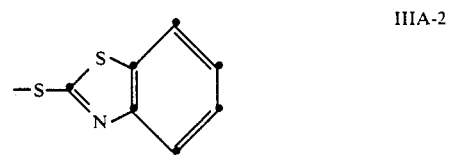

IIIA-2

IIIA-3 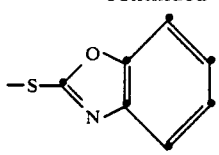

IIIA-4 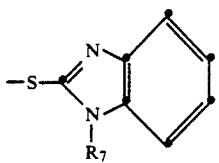

IIIA-5 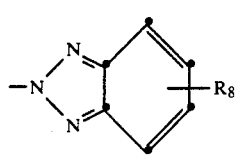

IIIA-6 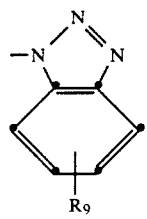

IIIA-7 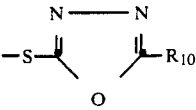

where $R_{10}$ is unsubstituted or substituted alkyl, such as butyl, 1-ethylpentyl, and 2-ethoxyethyl, or alkylthio, such as butylthio and octylthio; $R_6$ and $R_7$ are individually hydrogen, alkyl of 1 to 8 carbon atoms such as methyl, ethyl, or butyl, phenyl or substituted phenyl; and $R_8$ and $R_9$ are individually hydrogen or one or more halogen such as chloro, fluoro or bromo; alkyl of 1 to 4 carbon atoms, carboxyl, esters such as —COOCH$_3$, or other substituents such as —NHCOOCH$_3$, —SO$_2$OCH$_3$, —OCH$_2$CH$_2$SO$_2$CH$_3$,

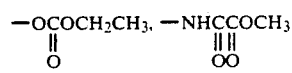

or nitro groups.

B. PUG's which are, or form, dyes upon release:

Suitable dyes and dye precursors include azo, azomethine, azopyrazolone, indoaniline, indophenol, anthraquinone, triarylmethane, alizarin, nitro, quinoline, indigoid and phthalocyanine dyes or precursors of such dyes such as leuco dyes, tetrazolium salts or shifted dyes. These dyes can be metal complexed or metal complexable. Representative patents describing such dyes are U.S. Pat. Nos. 3,880,658; 3,931,144; 3,932,380; 3,932,381 and 3,942,987. Preferred dyes and dye precursors are azo, azomethine and indoaniline dyes and dye precursors. Structures of some preferred dyes and dye precursors are:

IIIB-1 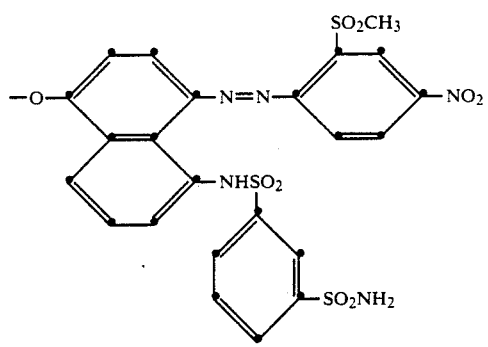

IIIB-2 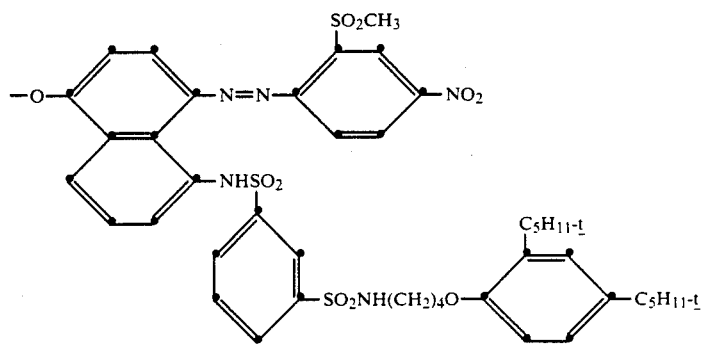

-continued

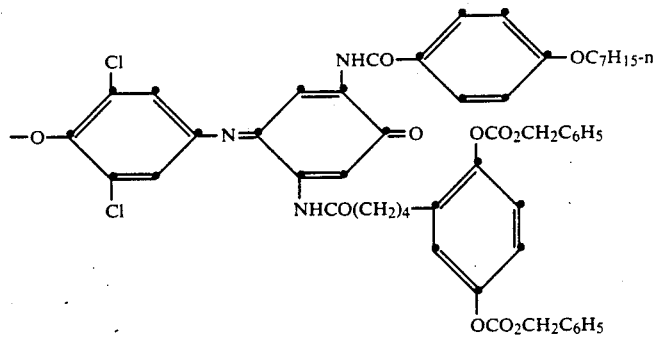
IIIB-3

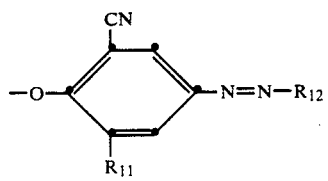
IIIB-4

| $R_{11}$ | $R_{12}$ |
|---|---|
| —H | 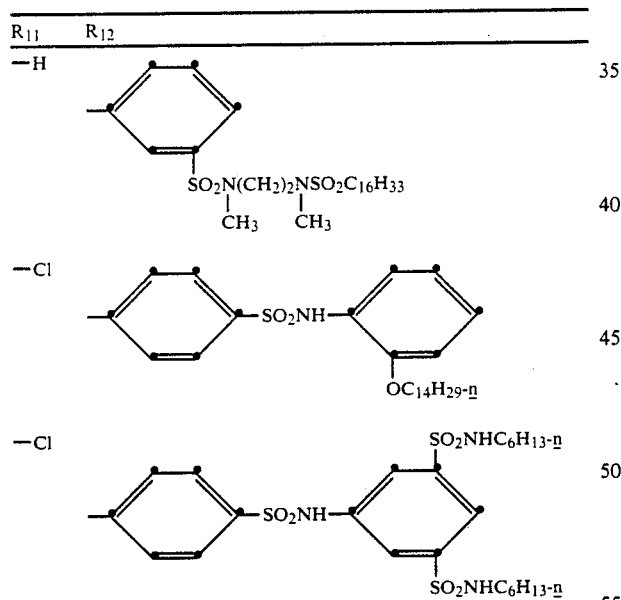 |
| —Cl | |
| —Cl | |

C. PUG's which are couplers:

Couplers released can be nondiffusible color-forming couplers, non-color forming couplers or diffusible competing couplers. Representative patents and publications describing competing couplers are: "On the Chemistry of White Couplers," by W. Püschel, Agfa-Gevaert AG Mitteilungen and der Forschungs-Laboratorium der Agfa-Gevaert AG, Springer Verlag, 1954, pp. 352–367; U.S. Pat. Nos. 2,998,314; 2,808,329; 2,689,793; 2,742,832; German Pat. No. 1,168,769 and British Pat. No. 907,274. Structures of preferred competing couplers are:

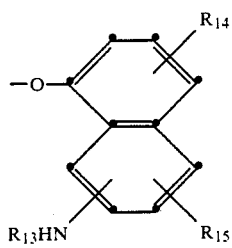
IIIC-1 where $R_{13}$ is hydrogen or alkylcarbonyl, such as acetyl, and $R_{14}$ and $R_{15}$ are individually hydrogen or a solubilizing group, such as sulfo, aminosulfonyl, and carboxy

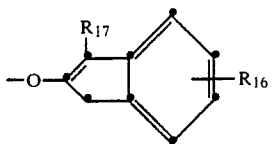
IIIC-2 where $R_{16}$ is hydrogen or a substituent that does not adversely affect the inhibitor, such as alkyl of 1 to 4 carbon atoms; $R_{17}$ is halogen, aryloxy, arylthio, or a development inhibitor, such as a mercaptotetrazole, such as phenylmercaptotetrazole or ethyl mercaptotetrazole.

D. PUG's which form developing agents:

Developing agents released can be color developing agents, black-and-white developing agents or cross-oxidizing developing agents. They include aminophenols, phenylene diamines, hydroquinones and pyrazolidones. Representative patents are: U.S. Pat. Nos. 2,193,015; 2,108,243; 2,592,364; 3,656,950; 3,658,525; 2,751,297; 2,289,367; 2,772,282; 2,743,279; 2,753,256 and 2,304,953.

Structures of preferred developing agents are:

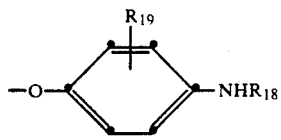

IIID-1 where R₁₈ is hydrogen or alkyl of 1 to 4 carbon atoms and R₁₉ is hydrogen or one or more halogen such as chloro or bromo; or alkyl of 1 to 4 carbon atoms such as methyl, ethyl or butyl groups.

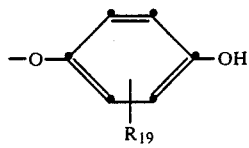

IIID-2 where R₁₉ is as defined above.

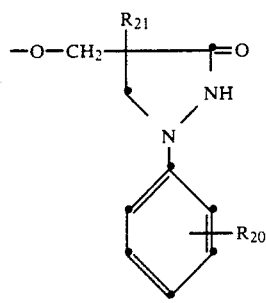

IIID-3

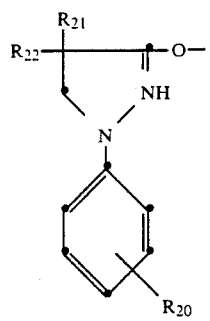

IIID-4

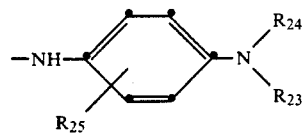

IIID-5

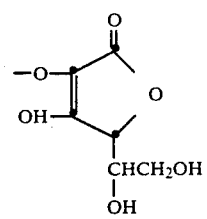

IIID-6 where R₂₀ is hydrogen or alkyl of 1 to 4 carbon atoms and R₂₁, R₂₂, R₂₃, R₂₄ and R₂₅ are individually hydrogen, alkyl of 1 to 4 carbon atoms such as methyl or ethyl; hydroxyalkyl of 1 to 4 carbon atoms such as hydroxymethyl or hydroxyethyl or sulfoalkyl containing 1 to 4 carbon atoms.

E. PUG's which are bleach inhibitors:

Representative patents are U.S. Pat. Nos. 3,705,801; 3,715,208; and German OLS No. 2,405,279. Structures of preferred bleach inhibitors are:

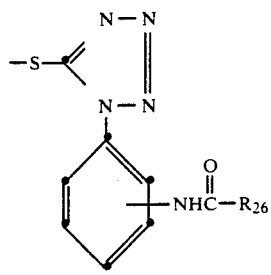

IIIE-1

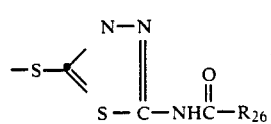

IIIE-2

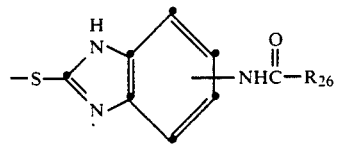

IIIE-3

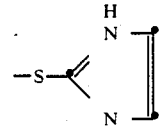

IIIE-4 where R₂₆ is alkyl such as alkyl of 6 to 20 carbon atoms.

F. PUG's which are bleach accelerators:

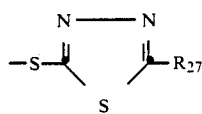

IIIF-1

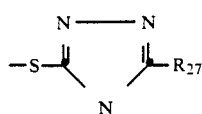

IIIF-2

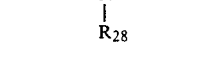

IIIF-3

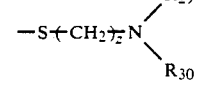

IIIF-4

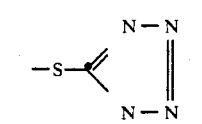

IIIF-5 wherein R₂₇ is hydrogen, alkyl, such as ethyl and butyl, alkoxy, such as ethoxy and butoxy, or alkylthio, such as ethylthio and butylthio, for example containing 1 to 6 carbon atoms, and which may be unsubstituted or substituted; R₂₈ is hydrogen, alkyl or aryl, such as phenyl; R₂₉ and R₃₀ are individually alkyl, such as alkyl containing 1 to 6 carbon atoms, for example ethyl and butyl; z is 1 to 6.

The photographic couplers of the invention can be incorporated in photographic elements by means and processes known in the photographic art. In a photographic element prior to exposure and processing the photographic coupler should be of such size and configuration that it will not diffuse through the photographic layers.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element. For example, a layer or unit affected by PUG can be controlled by incorporating in appropriate locations in the element a scavenger layer which will confine the action of PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an $\alpha$-olefin polymer, particularly a polymer of an $\alpha$-olefin containing 2 to 10 carbon atoms such as polyethylene, polypropylene, ethylene-butene copolymers and the like.

The compound (A), particularly photographic couplers as described, can be used in photographic elements in the same way as photographic couplers which release PUGs have previously been used in photographic elements. However, because of the improved ability to control the release of the PUG, the couplers permit enhanced effects or more selective effects. In addition, the couplers can be employed in applications where conventional couplers have previously been employed and a separate component was employed to provide a PUG.

Depending upon the nature of the particular PUG, the couplers can be incorporated in a photographic element for different purposes and in different locations.

When the PUG released from the coupler is a development inhibitor, the coupler can be employed in a photographic element like couplers which release development inhibitors have been used in the photographic art. Couplers of this invention which release a development inhibitor can be contained in, or in reactive association with, one or more of the silver halide emulsion units in a color photographic element. If the silver halide emulsion unit is composed of more than one layer, one or more of such layers can contain the coupler of this invention. The layers can contain other photographic couplers conventionally used in the art. The coupling reaction using couplers of this invention can form dyes of the same color as the color forming coupler(s) in the layer or unit, it can form a dye of a different color, or it can result in a colorless or neutral reaction product. The range of operation between layers of the development inhibitor released from the coupler of this invention can be controlled by the use of scavenger layers, such as a layer of fine grain silver halide emulsion. Scavenger layers can be in various locations in an element containing couplers of this invention. They can be located between layers, between the layers and the support, or over all of the layers.

Couplers of this invention which release development inhibitors can enhance the effects heretofore obtained with DIR couplers since they can release a development inhibitor at a distance from the point at which oxidized color developing agent reacted with the coupler, in which case they can provide, for example, enhanced interlayer interimage effects.

Photographic couplers as described which release bleach inhibitors or bleach accelerators can be employed in the ways described in the photographic art to inhibit the bleaching of silver or accelerated bleaching in areas of a photographic element.

Photographic couplers as described which release a dye or dye precursor can be used in processes where the dye is allowed to diffuse to an integral or separate receiving layer to form a desired image. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers as described can be employed to release another coupler and the PUG. If the released coupler is a dye-forming coupler it can react with oxidized developing agent in the same or an adjacent layer to form a dye of the same or a different color or hue as that obtained from the primary coupler. If the released coupler is a competing coupler it can react with oxidized color developing agent in the same or an adjacent layer to reduce dye density.

Photographic couplers as described in which the PUG is a developing agent can be used to release a developing agent which will compete with the color forming developing agent, and thus reduce dye density. Alternatively, the couplers can provide, in an imagewise manner, a developing agent which because of such considerations as activity would not desirably be introduced into the element in a uniform fashion.

In the following discussion of suitable materials for use in the emulsions and elements of this invention, reference will be made to Research Disclosure, December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-$\beta$-(methanesulfonamido)ethylaniline sulfate hydrate; 4-amino-3-methyl-N-ethyl-N-$\beta$-hydroxyethylaniline sulfate; 4-amino-3-$\beta$-(methanesulfonamido)ethyl-N,N-diethylaniline hydrochloride; and 4-amino-N-ethyl-N-(2-methoxyethyl)-m-toluidine di-p-toluenesulfonic acid.

The described photographic materials and processes can be used with photographic silver halide emulsions and addenda known to be useful in the photographic art, as described in, for example, Research Disclosure, December 1989, Item No. 308,119, the disclosures of which are incorporated herein by reference.

With negative working silver halide, the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Compounds as described can be prepared by reactions and methods known in the organic compound synthesis art. Typically, the couplers, as described, are prepared by first attaching the LINK group to the coupling position of the coupler moiety (COUP) without the PUG present. Then the product is reacted with an appropriate derivative of the PUG to form the coupler. Alternatively, the PUG may be attached first to the LINK group, and then the LINK-PUG group attached to the COUP. The following description illustrates these syntheses:

SYNTHESIS A

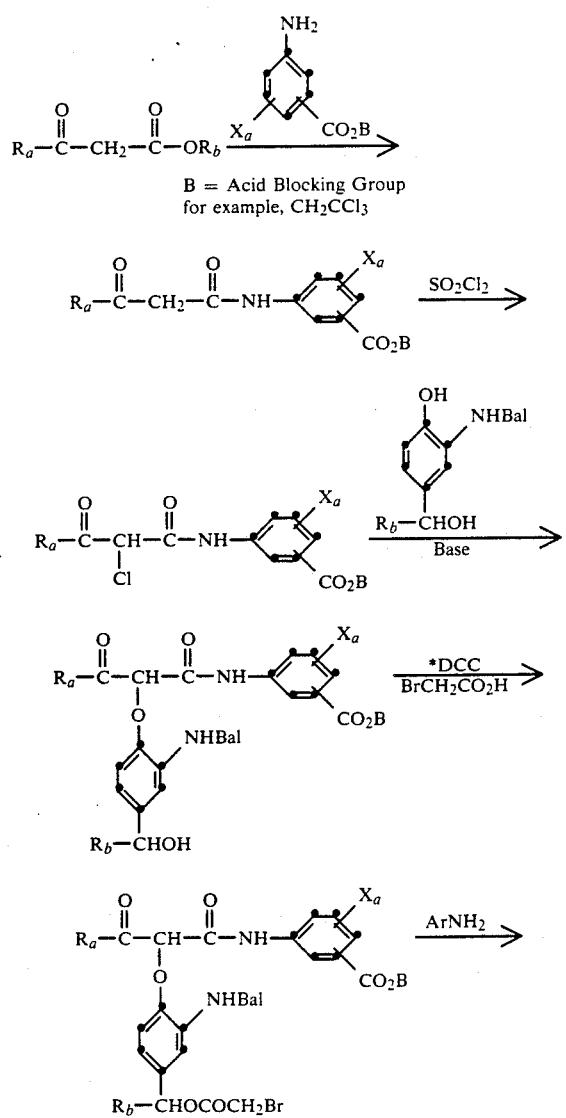

19

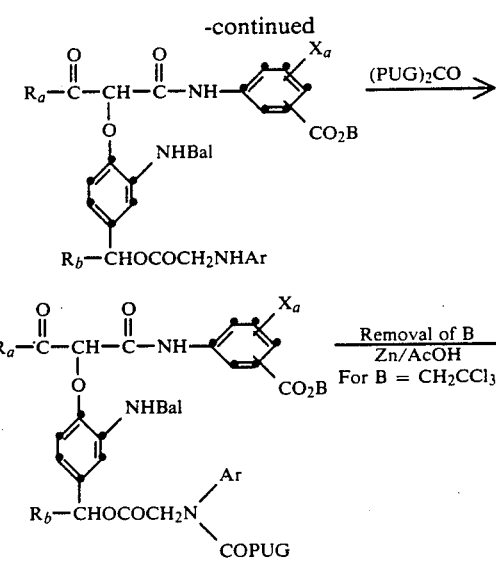

20

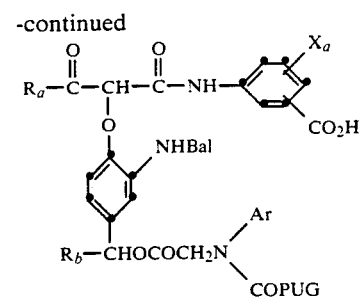

In the above Synthesis A:
 $R_a$ is an alkyl, such as a t-butyl group, or aryl, such as a p-methoxyphenyl group;
 B is an acidic blocking group, such as —$CH_2CCl_3$;
 Bal represents the atoms necessary to complete a ballast group, such as an alkylsulphonyl group containing 8 to 40 carbon atoms;
 $R_b$ is hydrogen or an alkyl group, such as methyl; and
 $X_a$ is hydrogen or a substituent group, such as chlorine, alkoxy or methyl.

SYNTHESIS EXAMPLE A

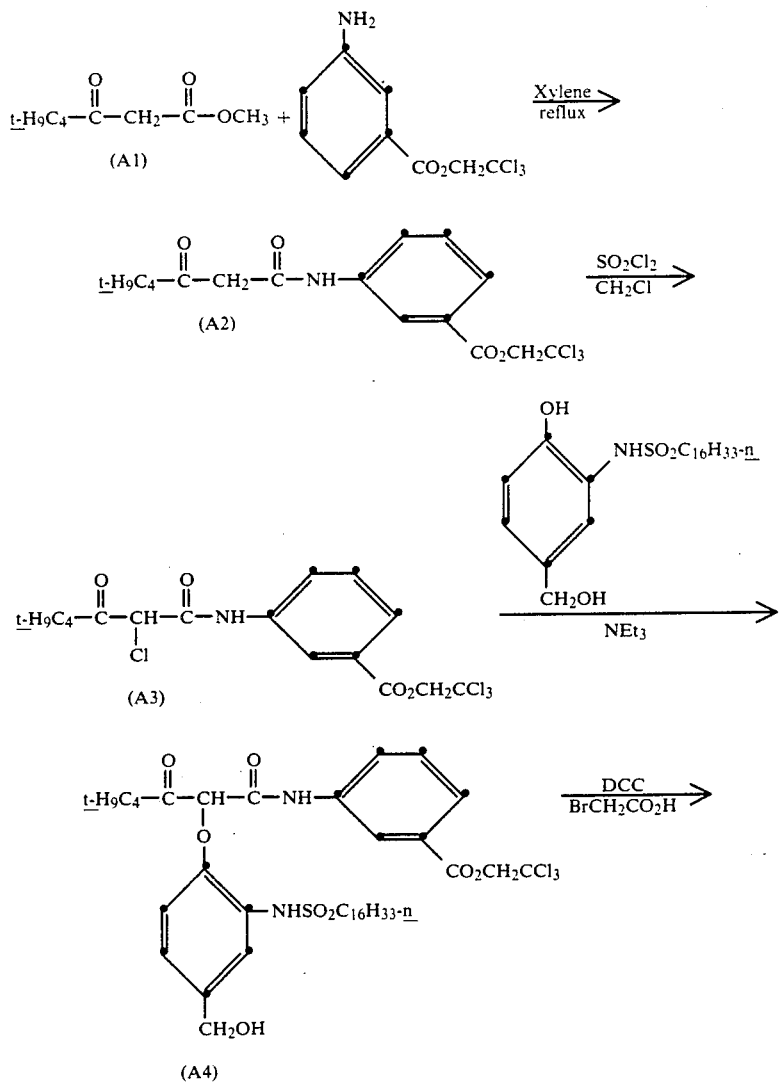

-continued

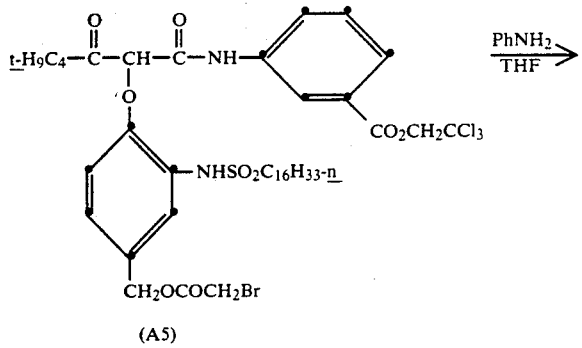
(A5)

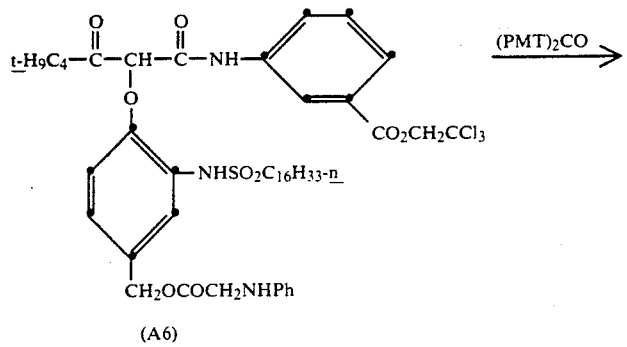
(A6)

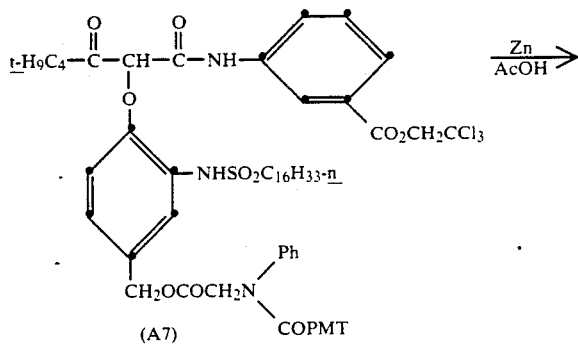
(A7)

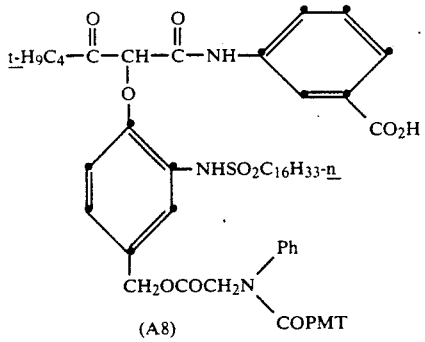
(A8)

Ph herein means phenyl.
PMT herein means phenylmercaptotetrazole.
Et herein means ethyl.
(PMT)$_2$CO herein means bis-phenylmercaptotetrazole, also described as bis-PMT-carbonyl.

COMPOUND (A2)

Methyl 4,4-dimethyl-3-oxovalerate (A1), (9.5 g, 59.58 mmol) together with 2',2',2'-trichloroethyl-3-aminobenzoate (16.0 g, 59.58 mmol) were taken up in xylene (200 mL) and heated to reflux. Xylene (100 mL) was distilled off via a Dean-Stark apparatus and a further batch of xylene (100 mL) added, and distilled off. The TLC (silica gel, 30% ethyl acetate in heptane) showed starting materials left with a significant amount of product. A further quantity of xylene (200 mL) was added and this, too, distilled off. The total time for the reaction to go to completion was about 2 hours. The reaction mixture was cooled, concentrated under reduced pressure, the residual oil taken up in 20% ethyl acetate in heptane and subjected to flash chromatography over silica gel eluting with the same solvent. The first major band was collected. Yield 20.0 g (85%).

COMPOUND (A3)

Compound (A2), (20.0 g, 50.67 mmol) was taken up in dry dichloromethane (100 mL) and stirred at room temperature under nitrogen. To this solution was then added sulphuryl chloride (4.3 mL, 53.21 mmol) in dichloromethane (20 mL) dropwise over a period of about 30 minutes. A TLC (silica gel, 20% ethyl acetate in heptane) showed no starting material after stirring at room temperature for a total period of 1 hour. The solvent was removed under reduced pressure to give the produce as an oil, yield 21.6 g (100%). This oil was pure enough to be taken on to the next step.

COMPOUND (A4)

2-Hydroxy-5-hydroxymethylbenzenehexadecylsulphonamide (15.0 g, 35.07 mmol) together with compound (A3), (18.1 g, 42.1 mmol) were taken up in dimethylformamide (100 mL) and stirred at room temperature. To this solution was added triethylamine (17.6 mL, 126.27 mmol) and the reaction stirred under nitrogen overnight. At the end of this period, a TLC (silica gel, 50% ethyl acetate in heptane) showed a nearly complete reaction. The reaction mixture was poured into ice cold 2N-HCl (800 mL) and the white solid filtered off, washed several times with acetonitrile and finally air dried. The filtrate contained some product which was isolated in the following manner. It was concentrated under reduced pressure, taken up in ethyl acetate, washed with 2N-HCl (X1), dried (MgSO$_4$), filtered and taken to an oil. This oil was taken up in 40% ethyl acetate in heptane and chromatographed over silica gel eluting with the same solvent mixture. The first major band was collected. The total yield of compound (A4), which includes the product isolated from the above residue and that from chromatographing the filtrate was 9.5 g (35%).

COMPOUND (A5)

Compound (A4), (9.5 g, 11.58 mmol) was taken up in dichloromethane (100 mL) and dicyclohexylcarbodiimide (2.63 g, 12.74 mmol) added, followed by bromoacetic acid (7.77 g, 12.74 mmol) and dimethylaminopyridine (100 mg). Almost immediately a precipitate of dicyclohexylurea began to form. The reaction was stirred at room temperature for 1 hour. A TLC of the reaction (50% ethyl acetate in heptane) showed complete reaction. The dicyclohexylurea was filtered off and the filtrate concentrated under reduced pressure to give an oil which was not purified any further but used as such in the next step. Yield of compound (A5) 100%.

COMPOUND (A6)

Compound (A5), (11.58 mmol) was taken up in tetrahydrofuran (75 mL). To this solution was added aniline (10.75 mL, 115.8 mmol) and the reaction stirred at room temperature overnight under a nitrogen atmosphere. At the end of this reaction period a TLC (40% ethyl acetate in heptane) showed one major new spot. The solvent was removed under reduced pressure and the oil taken up in ethyl acetate. This solution was washed with 2N-HCl (X3), dried (MgSO$_4$), filtered and taken to an oil under reduced pressure. This product compound (A6) was pure enough for the next step. Yield 100%.

COMPOUND (A7)

Compound (A6), (11.58 mmol) was taken up in tetrahydrofuran (75 mL) to which was added bis-PMT-carbonyl, (4.87 g, 12.74 mmol). The resulting solution was stirred at room temperature for approximately 2 hours, after which time a TLC (silica gel, 40% ethyl acetate in heptane) showed a little starting material left. A further batch of the bis-PMT-carbonyl (0.45 g, total 5.31 g, 13.90 mmol) was added and the reaction stirred at room temperature for a further 1 hour. At the end of this period the solvent was removed under reduced pressure and the residual oil taken up in ethyl acetate. This ethyl acetate was then washed with 5% NaHCO$_3$ (X3), dried (MgSO$_4$), filtered and taken to an oil under reduced pressure. This oil was taken up in 30% ethyl acetate in heptane (100 mL) and subjected to flash chromatography eluting with the same solvent mixture. The first major band was collected. Two fractions were collected, the first gave 2.0 g and the second 6.2 g. The former contained a trace of impurity and was not used in the subsequent unblocking reaction, while the latter was pure and used in the next step. Yield compound (A7), 46% based on the pure material only.

COMPOUND (A8)

Compound (A7), (6.2 g, 5.36 mmol) was taken up in acetic acid (50 mL) and stirred at room temperature. To this solution was added zinc dust, (11.0 g) and stirring continued for approximately 15 minutes. A TLC (silica gel, ethyl acetate or 10% tetrahydrofuran in ethyl acetate) showed no starting material, just one major product spot. The excess zinc dust and inorganic salts were filtered off over celite and the acetic acid removed under reduced pressure. The residual oil was taken up in ethyl acetate, washed with 2.5%-NaHCO$_3$ and dried over MgSO$_4$. On filtering and removal of the ethyl acetate the product, compound (A8) was obtained. Yield 5.5 g (100%).

Calculated for $C_{53}H_{67}ClN_7O_{10}S_2 \cdot 2CH_3CO_2H$: %C=59.7, %H=6.6, %N=8.6, %S=5.6. Found: %C=60.0, %H=6.3, %N=9.2, %S=5.5.

SYNTHESIS B

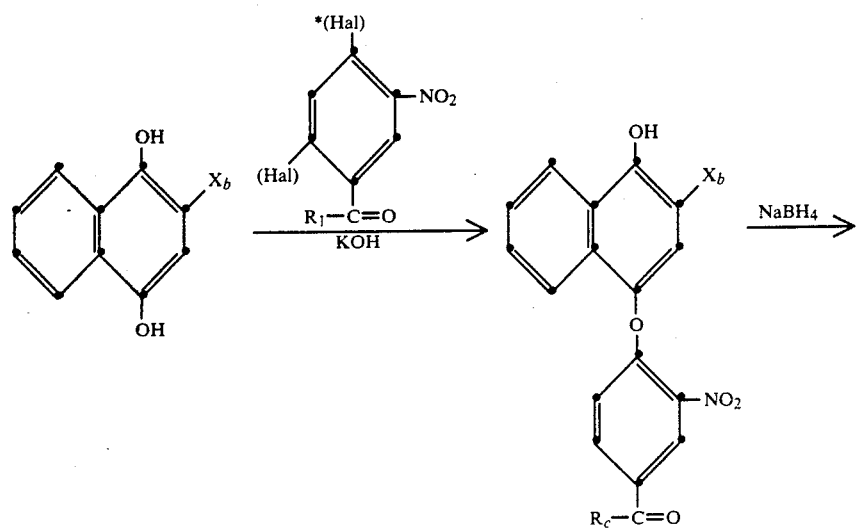
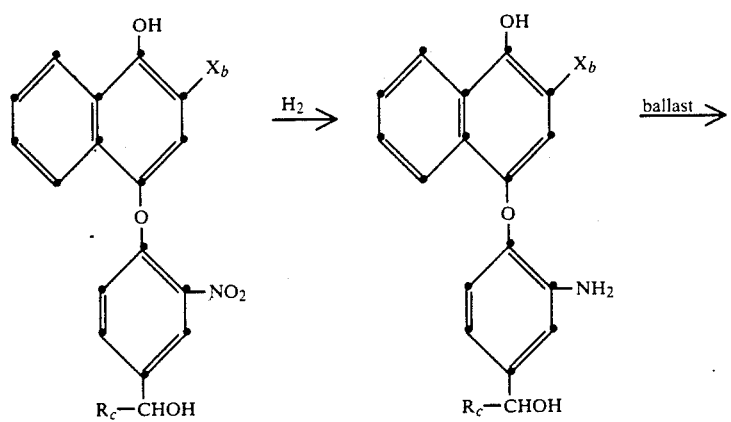
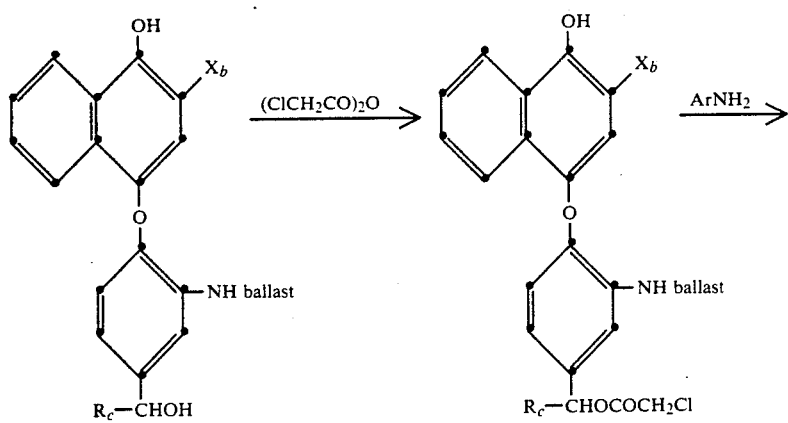

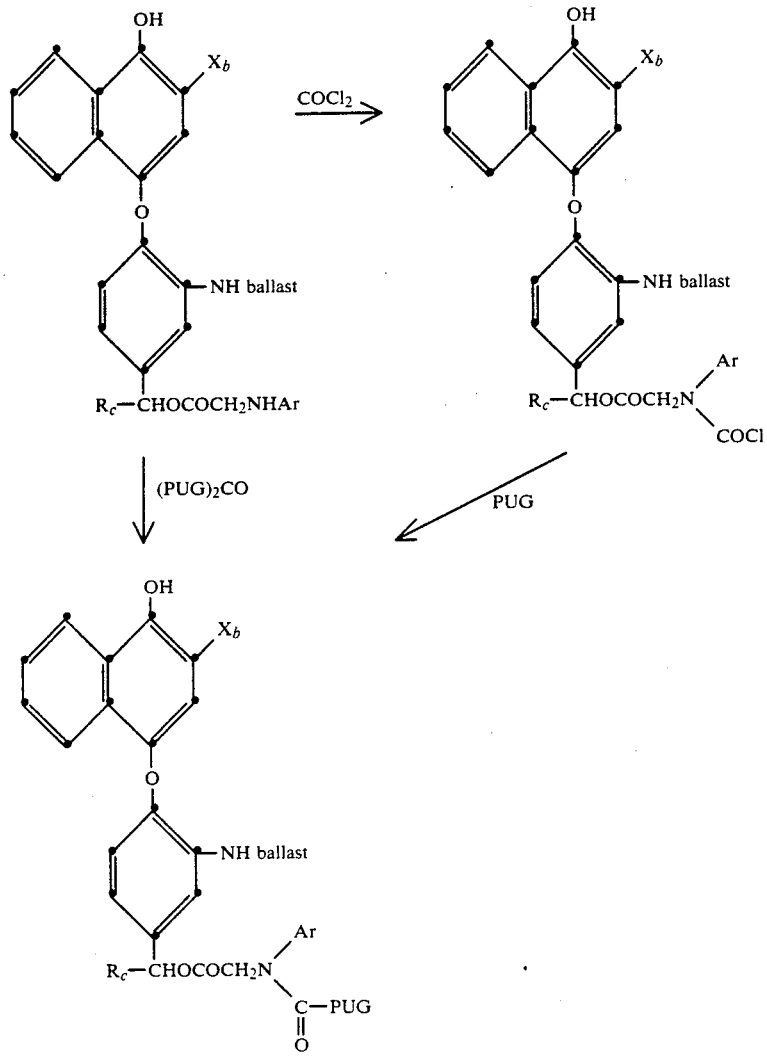

*Hal herein is halogen.

In the above Synthesis B:

$X_b$ is a group that enables the resulting coupler upon oxidative coupling to form a dye that is capable of being washed out of a photographic element upon processing, such as —CONHCH$_3$ or —CONHCH$_2$CH$_3$; and $R_c$ is hydrogen, unsubstituted or substituted alkyl, such as methyl, aryl, or ballast group;

ballast is a compound that contains a ballast group as described, such as a group containing an alkyl group of 8 to 40 carbon atoms.

The Synthesis B can be carried out as described and illustrated with the resulting group comprising the PUG being in the position para to the oxygen of the illustrated phenoxy coupling-off group or, optionally, the Synthesis B can be carried out by changing the location of the illustrated NH ballast group and changing the resulting group comprising the PUG to the position ortho to the oxygen atom of the illustrated phenoxy coupling-off group.

The following is an example illustrating preparation of a coupler according to Synthesis B:

SYNTHESIS EXAMPLE B

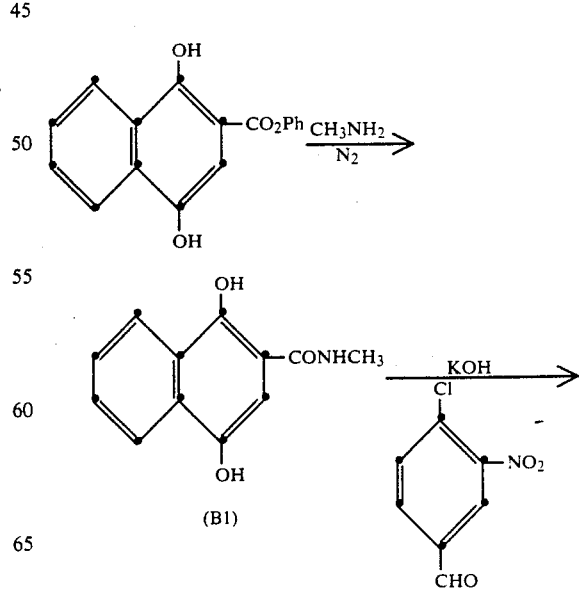

-continued
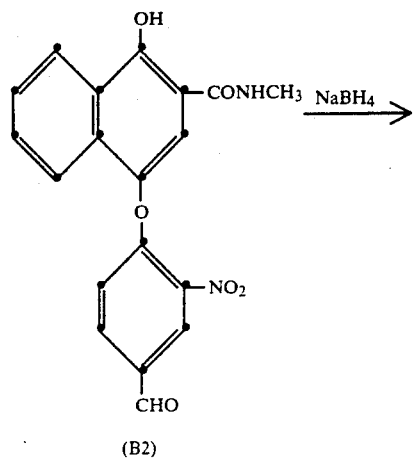
(B2)
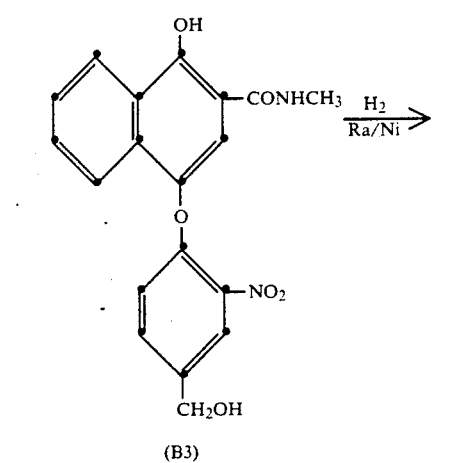
(B3)
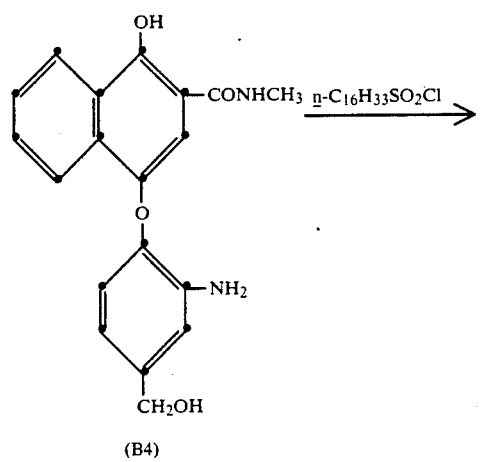
(B4)
-continued
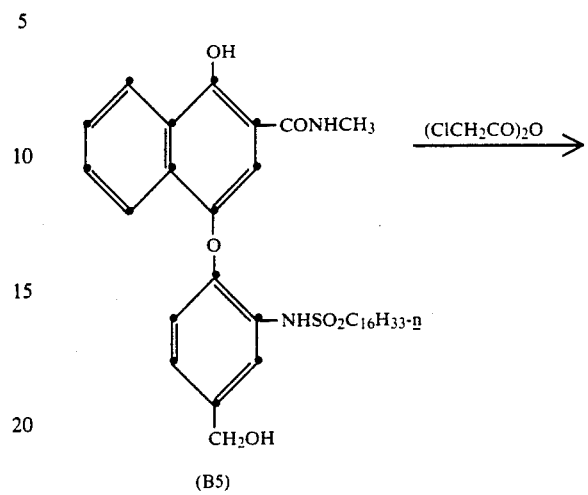
(B5)
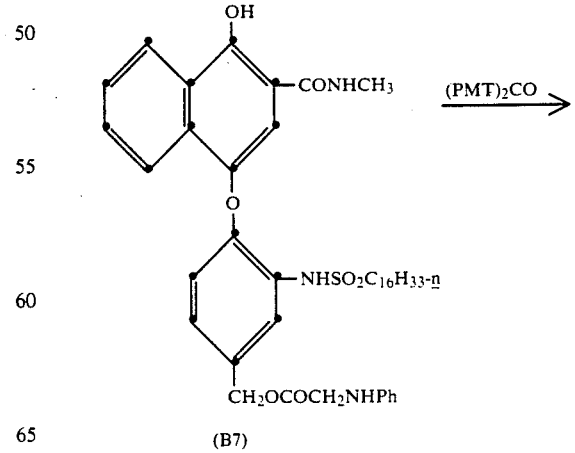
(B6)
(B7)

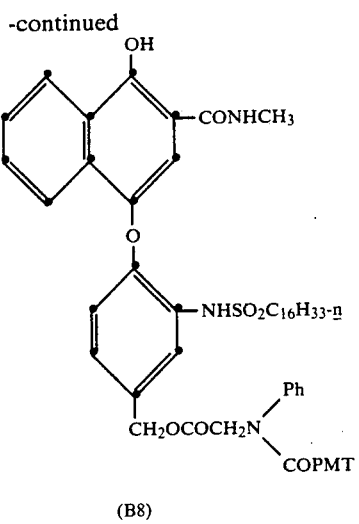

(B8)

COMPOUND (B1)

Phenyl 1,4-dihydroxy-2-naphthoate (30.0 g, 0.107 mol) was taken up in deoxygenated tetrahydrofuran (300 mL). Under a nitrogen atmosphere, 40% aqueous methylamine (35 mL, 0.451 mol) was added dropwise over a 15 minute period. The resulting solution was stirred for 1 hour while under the nitrogen atmosphere. At the end of this period the reaction was then poured into ice cold 2N-HCl (2.5 L) and the precipitate filtered off, washed well with water and air dried. This material was pure enough to be used in the next step. Yield 23.0 g (99%).

COMPOUND (B2)

Compound (B1) (50.0 g, 230.2 mmol) was taken up in deoxygenated dimethylformamide (500 mL) to which was added 85%-potassium hydroxide (38.0 g, 575.4 mmol) followed by deoxygenated water (50 mL) and the solution stirred at room temperature for about 15 minutes under a nitrogen atmosphere. At the end of this period all of the potassium hydroxide had dissolved to give a dark yellow-red colored solution. To this solution was then added 4-chloro-3-nitrobenzaldehyde (47.0 g, 253.2 mmol) as a solid, all at once. The reaction mixture was then stirred at room temperature for approximately 1 hour after which a TLC (silica gel, 1% acetic acid in ethyl acetate or 1% acetic acid in 50% ethyl acetate in heptane) showed a single major spot with only traces of starting materials left. The reaction was poured into ice cold 2N-HCl (3.0 L) with stirring. The produce oiled out and was collected by decanting off the aqueous layer. The oil was then taken up in ethyl acetate and treated with heptane. The dark colored solid was collected and recrystallized from a mixture of acetonitrile (400 mL) and water (200 mL). After drying, 26.0 g of compound (B2) was obtained, yield 31%.

COMPOUND (B3)

Compound (B2) (26.0 g, 70.97 mmol) was taken up in tetrahydrofuran (150 mL). Methanol (50 mL) and water (25 mL) were added followed by the portionwise addition of sodium borohydride (2.68 g, 70.97 mmol). After the addition was complete and the solution stirred at room temperature for 15 minutes, a TLC (silica gel, 1% acetic acid in 50% ethyl acetate in heptane) indicated the reaction was complete with only one major product formed. The reaction mixture was concentrated under reduced pressure, the residue was taken up in ethyl acetate and washed with 2N-HCl (X3). The ethyl acetate layer was then dried (MgSO4), the solvent removed under reduced pressure and treated with heptane to give compound (B3). Yield 20.6 g (79%).

COMPOUND (B4)

Compound (B3) (20.6 g, 70.97 mmol) was dissolved in methanol (500 mL) and Raney-Nickel (a few scoops of material which had been pre-washed with water and methanol) was added. The mixture was then hydrogenated under a hydrogen atmosphere of 55 psi. When hydrogen up-take had ceased, the hydrogenation was stopped and the catalyst filtered off. The solvent was removed under reduced pressure and the crude material so obtained was used as such in the next step of the reaction sequence. A yield of 100% was assumed for compound (B4).

COMPOUND (B5)

Compound (B4) (70.97 mmol) was taken up in dry pyridine (250 mL) and hexadecylsulfonyl chloride (25.4 g, 78.16 mmol) was added all at once and the resulting solution stirred at room temperature for 30 minutes. After this time a TLC (silica gel, 50% ethyl acetate in heptane) showed complete reaction. The reaction mixture was concentrated under reduced pressure, taken up in ethyl acetate and washed with 2N-HCl (X3). The organic layer was dried (MgSO4), then filtered and taken to an oil under reduced pressure. This oil crystallized from acetonitrile. The product, compound (B5), was filtered off and air dried. Yield 20.0 g (45%).

COMPOUND (B6)

Compound (B5) (5.0 g, 7.89 mmol) was dissolved in tetrahydrofuran (50 mL) to which was added chloroacetic anhydride (2.18 g, 12.76 mmol) followed by pyridine (1.03 mL, 12.76 mmol) and the reaction stirred at room temperature for 15 minutes. A TLC (silica gel, 40% ethyl acetate in heptane) showed mainly product with a little of compound (B5) still present. Further batches of chloroacetic anhydride (200 mg) and pyridine (0.1 mL) were then added which took the reaction to completion after stirring another 15 minutes. The solvent was removed under reduced pressure, the residual oil taken up in ethyl acetate, washed with 2N-HCl (X3), dried (MgSO4), filtered and then concentrated to an oil again. This oil crystallizes from acetonitrile to give compound (B6). The crude product from this reaction was used as such in the next step.

COMPOUND (B7)

Compound (B6) (7.98 mmol) was taken up in dimethylformamide (50 mL). To this was then added potassium iodide (1.32 g, 7.98 mmol) and aniline (2.2 mL, 23.93 mmol) and the mixture then stirred and heated to 60° C. for 2 hours. The reaction mixture was then cooled, poured into 2N-HCl and extracted with ethyl acetate. The ethyl acetate layer was collected, washed further with 2N-HCl (X3), then dried (MgSO4), filtered and then taken to an oil under reduced pressure. This oil crystallizes from methanol or acetonitrile. Yield 3.6 g (59%).

COMPOUND (B8)

Compound (B7) (6.1 g, 8.03 mmol) was dissolved in tetrahydrofuran (70 mL). To this solution was then added bis-PMT-carbonyl (3.1 g, 8.03 mmol) and the resulting solution was stirred at room temperature for 3 hours. A TLC (silica gel, 50% ethyl acetate in heptane) showed there to be some compound (B7) still present. A further batch of bis-PMT-carbonyl (300 mg, total 3.38 g, 8.83 mmol) was then added and stirring at room temperature continued overnight. At the end of this period the reaction solution was concentrated under reduced pressure, taken up in ethyl acetate and washed with 2.5N-$Na_2CO_3$ (X1), brine (X1), 2N-HCl (X1), dried ($MgSO_4$) and filtered. The filtrate was concentrated to an oil under reduced pressure, taken up in 40% ethyl acetate in heptane and subjected to flash chromatography eluting with the same solvent mixture. The first major band was collected. Yield 7.2 g (93%).

Calculated for $C_{51}H_{61}N_7O_8S_2$: %C=63.53, %H=6.38, %N=10.17, %S=6.65. Found: %C=63.30, %H=6.43, %N=10.02, %S=6.37.

The following couplers are illustrative of couplers prepared by the described methods:

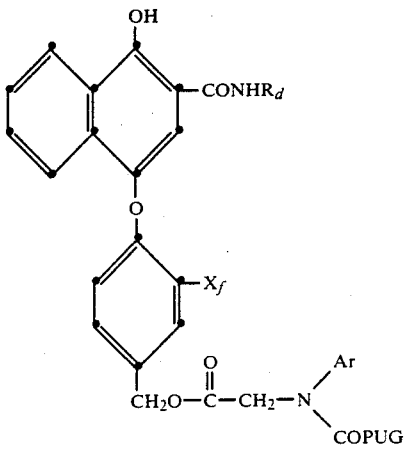

| Cmpd No. | $R_d$ | $X_f$ | Ar | PUG |
|---|---|---|---|---|
| 1 | —$CH_3$ | $NHSO_2C_{16}H_{33}$-n | Ph | PMT |
| 2 | —$CH_3$ | $NHSO_2C_4H_9$-n | Ph | PMT |
| 3 | —$CH_3$ | $NHSO_2C_{16}H_{33}$-n | Ph | tetrazolylthio-$CH_2CO_2C_3H_7$-n |
| 4 | —$CH_3$ | $NHSO_2C_{16}H_{33}$-n | Ph | tetrazolylthio-$CH_2CO_2C_4H_9$-n |
| 5 | —$CH_3$ | $NHSO_2C_{16}H_{33}$-n | Ph | tetrazolylthio-$CH_2$-C$_6$H$_4$-$OCH_3$ |
| 6 | —$CH_2CH_2CH_3$ | $NHSO_2C_{16}H_{33}$-n | Ph | PMT |
| 7 | —$CH_2CH_3$ | $NHSO_2C_{16}H_{33}$-n | Ph | PMT |
| 8 | —$CH_2CH_2OCH_3$ | $NHSO_2C_{16}H_{33}$-n | Ph | PMT |

-continued
| | | | | |
|---|---|---|---|---|
| 9 | —CH$_2$CH$_2$OCH$_3$ | NHSO$_2$C$_{16}$H$_{33}$-n | Ph | 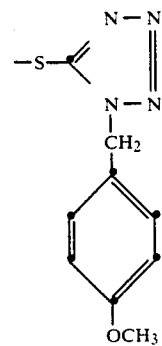 |
| 10 | —(CH$_2$)$_4$CH$_3$ | NHSO$_2$C$_{16}$H$_{33}$-n | Ph | PMT |
| 11 | —(CH$_2$)$_4$CH$_3$ | NHSO$_2$C$_{16}$H$_{33}$-n | Ph | 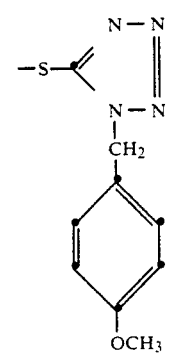 |
| 12 | 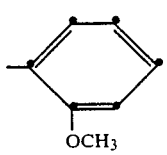 | NHSO$_2$C$_{16}$H$_{33}$-n | Ph | PMT |
| 13 | —CH$_3$ | NHSO$_2$C$_{16}$H$_{33}$-n | 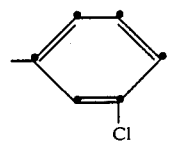 | PMT |
| 14 | —CH$_3$ | NHSO$_2$C$_{16}$H$_{33}$-n | 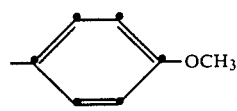 | PMT |
| 15 | —CH$_2$CO$_2$C$_2$H$_5$ | NHSO$_2$C$_{16}$H$_{33}$-n | Ph | PMT |
| 16 | 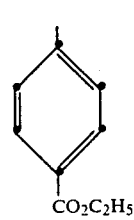 | 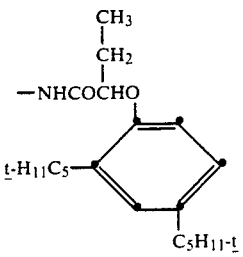 | Ph | PMT |

-continued

| | | | | |
|---|---|---|---|---|
| 17 | 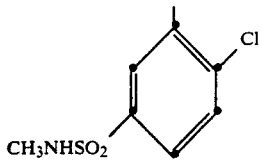<br>CH$_3$NHSO$_2$ | 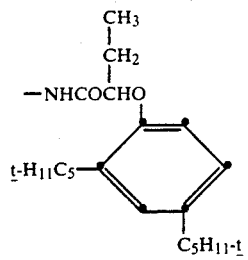<br>—NHCOCHO with CH$_3$CH$_2$ group, t-H$_{11}$C$_5$ and C$_5$H$_{11}$-t substituents | Ph | PMT |
| 18 | 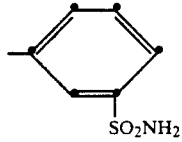<br>SO$_2$NH$_2$ | —NHCOC$_{11}$H$_{23}$-n | Ph | PMT |

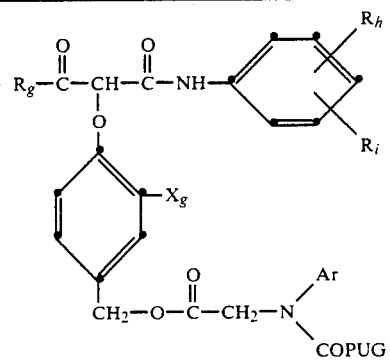

| Cmpd No. | R$_g$ | R$_h$ | R$_i$ | X$_g$ | Ar | PUG |
|---|---|---|---|---|---|---|
| 19 | t-C$_4$H$_9$ | H | 3-CO$_2$H | NHSO$_2$C$_{16}$H$_{33}$-n | Ph | PMT |
| 20 | t-C$_4$H$_9$ | 2-Cl | 5-CO$_2$H | NHSO$_2$C$_{16}$H$_{33}$-n | Ph | PMT |
| 21 | t-C$_4$H$_9$ | H | 4-CO$_2$H | NHSO$_2$C$_{16}$H$_{33}$-n | Ph | PMT |
| 22 | 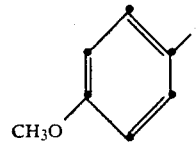<br>CH$_3$O | H | 3-CO$_2$H | NHSO$_2$C$_{16}$H$_{33}$-n | Ph | PMT |
| 23 | t-C$_4$H$_9$ | 2-Cl | 5-NHSO$_2$CH$_3$ | NHSO$_2$C$_{16}$H$_{33}$-n | Ph | PMT |

The release of a useful compound from a carrier compound (A) can also be useful in other applications wherein controlled release is desired. Initiation of such release can be triggered by hydrolysis or redox reactions, for example. For example, the described LINK-PUG group can release, for example, pharmaceutically useful moieties, including drugs, dyes, analytical agents, agricultural chemicals, and other useful moieties.

The following examples further illustrate the invention:

EXAMPLES 1-21

Photographic elements were prepared by coating the following layers on a cellulose ester film support (amounts of each component are indicated in mg/m²):

Emulsion layer 1: Gelatin—2420; red sensitized silver bromoiodide (as Ag)—1615; yellow image coupler dispersed in dibutyl phthalate (RECEIVER LAYER)

Interlayer: Gelatin—860; didodecylhydroquinone—113

Emulsion layer 2: Gelatin—2690; green sensitized silver bromoiodide (as Ag)—1615; magenta image coupler dispersed in tritolyl phosphate; DIR compound of Table 1 dispersed in N,N-diethyl-dodecanamide and coated at a level sufficient to provide a contrast of 0.5 (half) of the original contrast after stepwise green light exposure and processing. (CAUSER LAYER)

Protective Overcoat: Gelatin—5380; bisvinylsulfonylmethyl ether at 2% total gelatin.

Structures of the image couplers are as follows:

Magenta Image Coupler

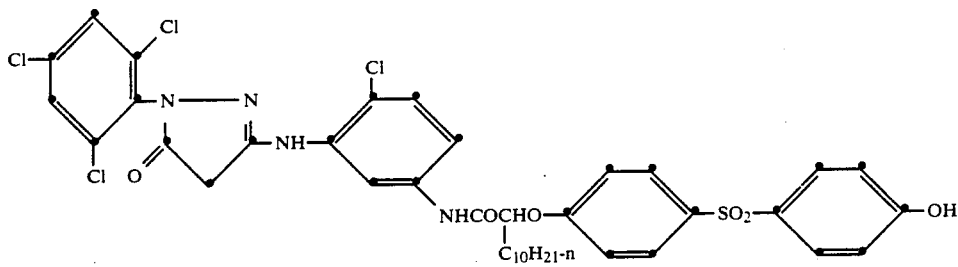

Yellow Image Coupler

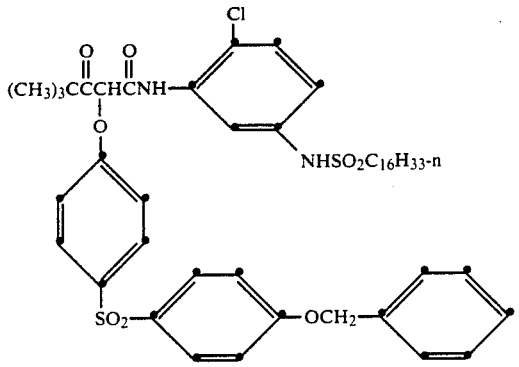

Strips of each element were exposed to green light through a graduated density step tablet, or through a 35% modulation fringe chart for sharpness measurements, and then developed 3.25 minutes at 38° C. in the following color developer, stopped, washed, bleached, fixed, washed and dried.

Color Developer

| | |
|---|---|
| Distilled water | 800 mL |
| Sodium Metabisulfite | 2.78 g |
| Sodium Sulfite, anhydrous | 0.38 g |
| CD-4 (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate (HAS) | 2.41 g |
| Diethylenetriaminepentacetic acid, pentasodium salt (40% Soln.) | 8.43 g |
| Distilled water | to 1 L |
| Adjust pH to 10.0. | |

*CD-4 is 4-amino-3-methyl-N-ethyl-N-beta-hydroxy-ethylaniline sulfate.

Processed images were read with green light to determine the contrast and AMT acutance. From plots of AMT acutance vs. the logarithm of the contrast for variations in the coated level of each development inhibitor releasing (DIR) compound, the acutance was determined at a contrast of 0.5 compared to its original contrast without the presence of the DIR compound. The acutance for the control DIR coupler was subtracted from each AMT value to provide the relative sharpness value reported as change in AMT in Table I. AMT calculations employed the following formula in which the cascaded area under the system modulation curve is shown in equation (21.104) on page 629 of the "Theory of the Photographic Process", 4th Edition, 1977, edited by T. H. James: AMT $=100+66\text{Log}[\text{cascaded area}/2.6696M]$ wherein the magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009–12, (1973). AMT is a further modification of CMT useful for evaluating systems which include the viewing of a positive print made from a negative.

Interimage effect (the degree of color correction) was evaluated after a daylight exposure. Interimage effect, as reported in Table I, was quantified as the ratio of the gamma of the green-sensitive layer (causer) to that of the red-sensitive layer (receiver).

TABLE I

| Example No./DIR Coupler No. | Change in AMT | Gamma Causer Gamma Receiver |
|---|---|---|
| Cntrl DIR Cplr | 0 | 1.0 |
| 1 | 2.6 | 2.5 |
| 2 | 2.6 | 3.1 |
| 3 | 5.6 | 2.1 |
| 4 | 4.4 | 1.9 |
| 5 | 3.4 | 2.2 |
| 6 | 1.6 | 2.0 |
| 7 | 8.5 | 2.2 |
| 8 | 3.1 | 2.3 |
| 9 | 3.1 | 2.5 |
| 10 | 4.0 | 1.5 |
| 11 | 4.0 | 1.8 |
| 12 | 3.7 | 1.5 |
| 13 | 4.1 | 1.5 |
| 14 | 2.7 | 1.2 |
| 15 | 3.4 | 2.7 |
| 16 | 4.7 | 2.4 |
| 17 | 3.1 | 3.1 |
| 18 | 4.0 | 2.4 |
| 19 | 3.5 | 2.4 |

TABLE I-continued
| | | |
|---|---|---|
| 20 | 3.5 | 2.6 |
| 21 | 3.1 | 2.5 |
| *C-1 (Comparison) | 3.6 | 2.8 |
| | (No wash-out of dye formed) | |
| C-2 (Comparison) | 0 | 1.8 |
| C-3 (Comparison) | 0 | 1.8 |
*Comparison wherein the image coupler was the following:
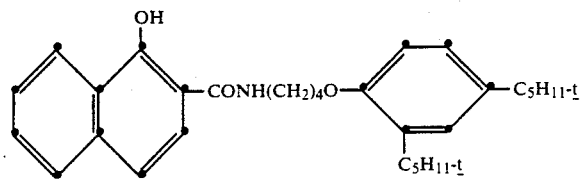
| | | |
|---|---|---|
| C-4 (Comparison) | 0 | 1.7 |
| C-5 (Comparison) | 2.3 | 2.7 |
| | (coupler causes undesired wandering in the layer) | |
Control DIR Coupler:
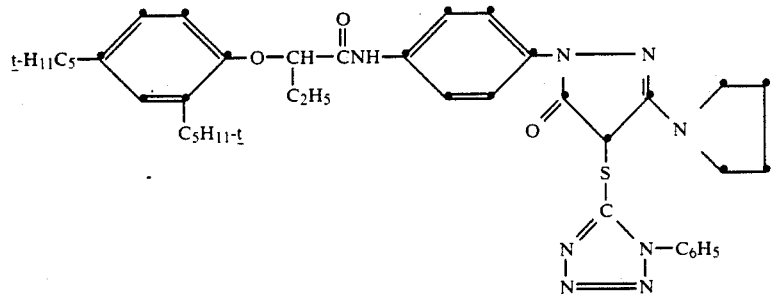
Coupler 1
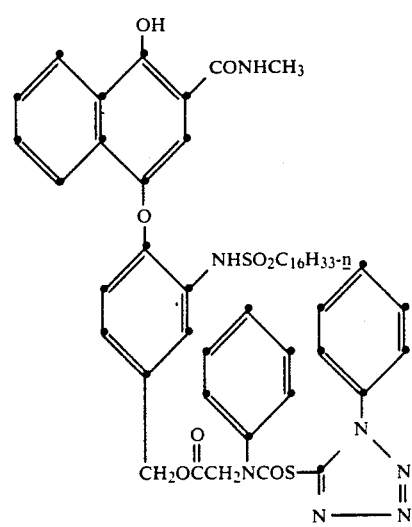
Coupler 2

TABLE I-continued
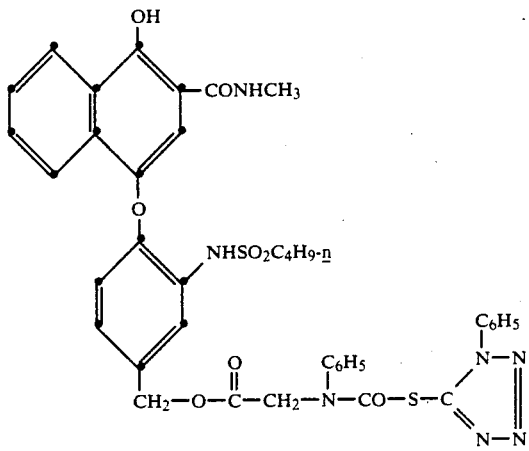
Coupler 3
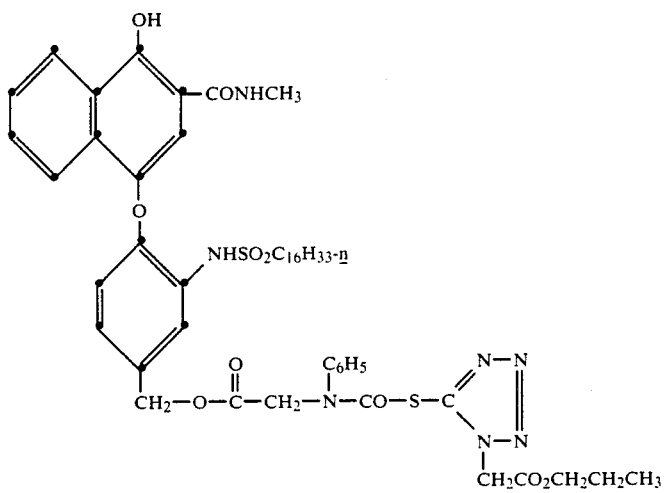
Coupler 4
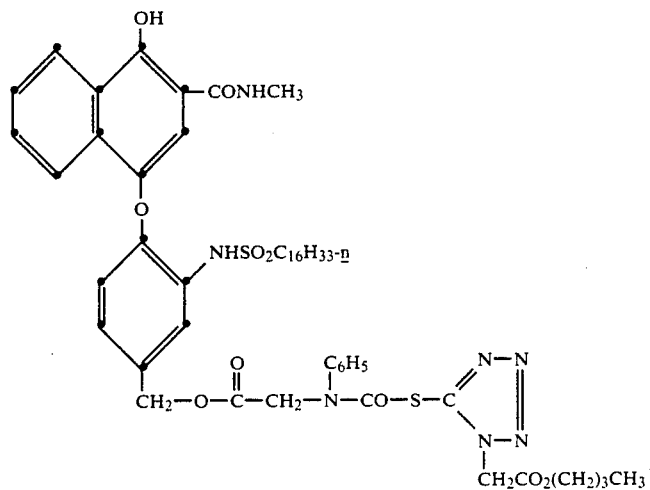
Coupler 5

TABLE I-continued
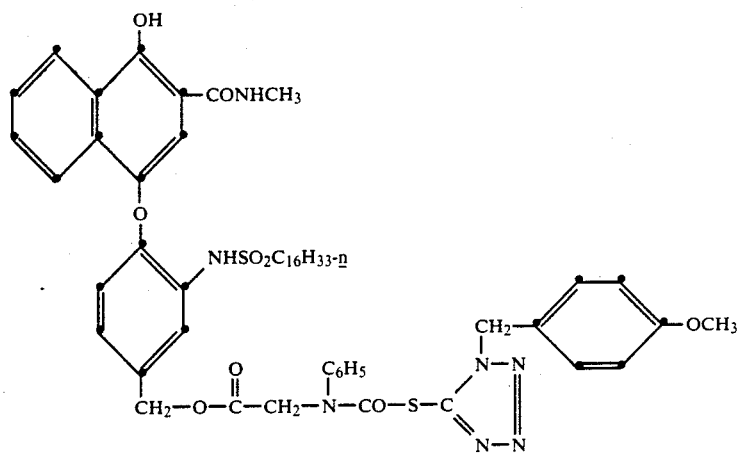
Coupler 6
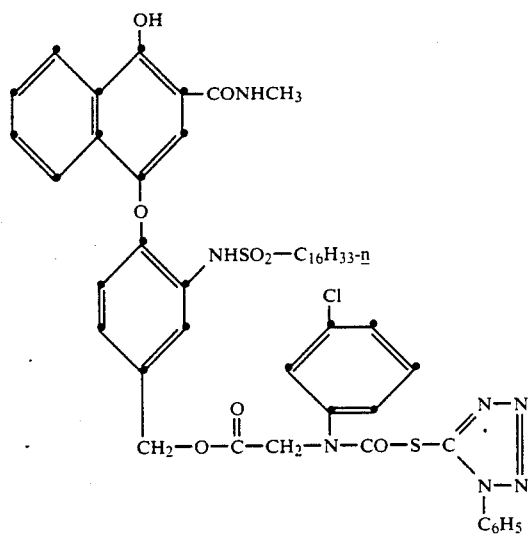
Coupler 7
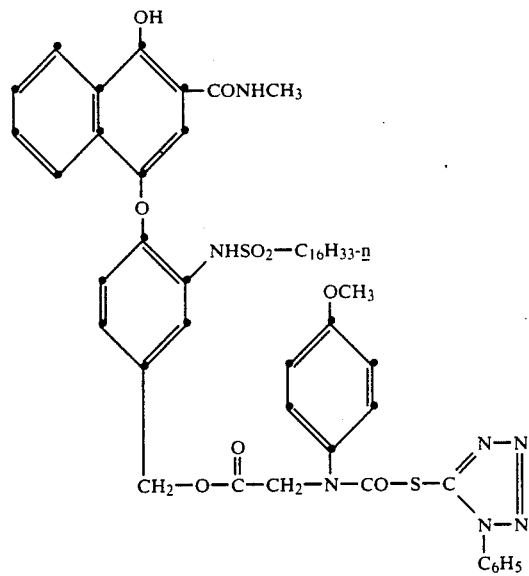
Coupler 8

TABLE I-continued
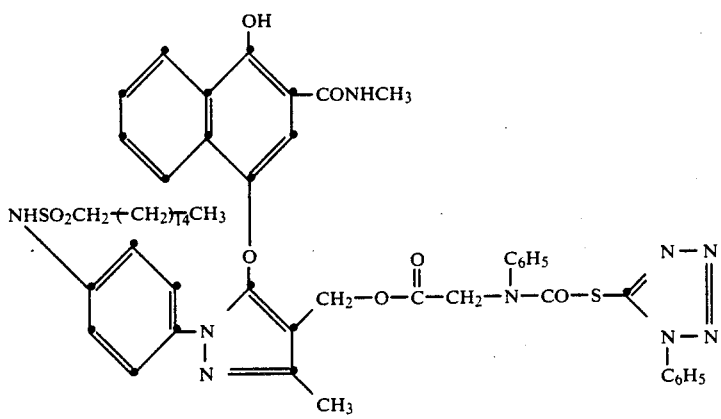
Coupler 9
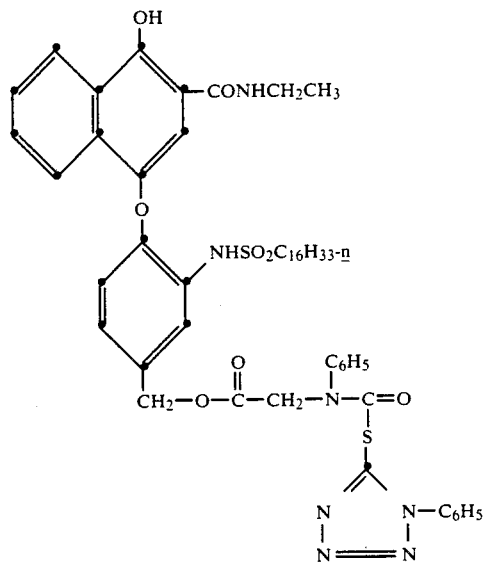
Coupler 10
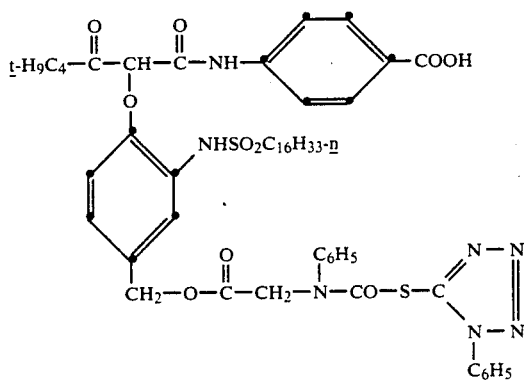
Coupler 11

TABLE I-continued
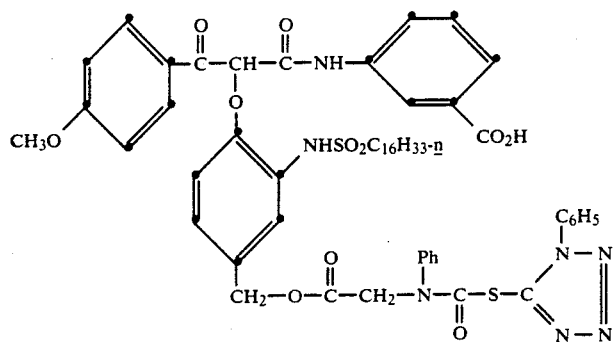
Coupler 12
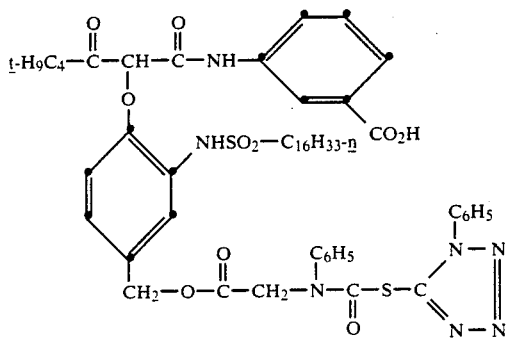
Coupler 13
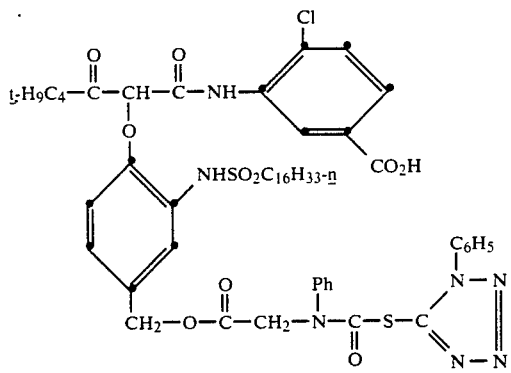
Coupler 14
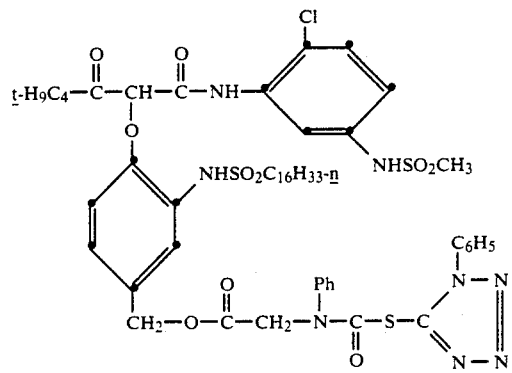
Coupler 15

TABLE I-continued
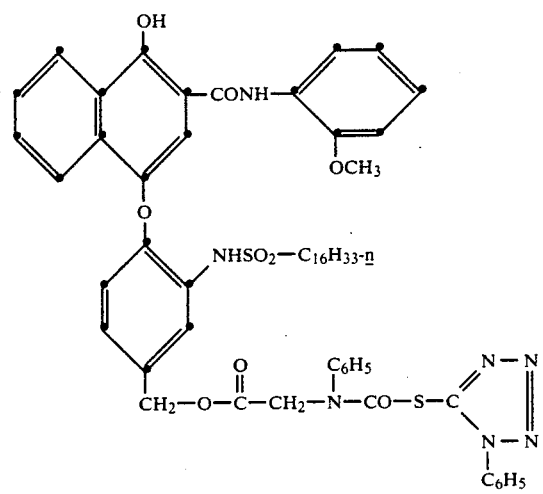
Coupler 16
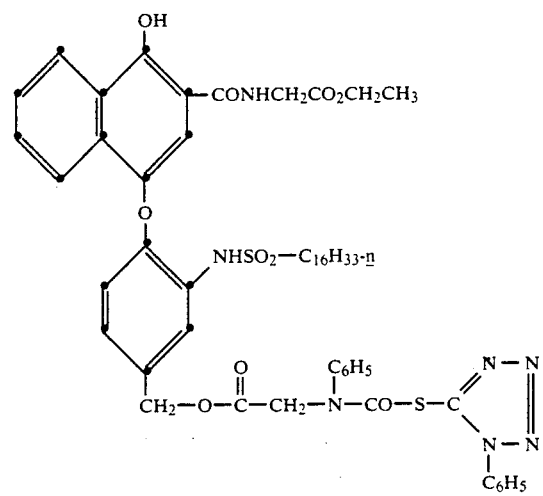
Coupler 17
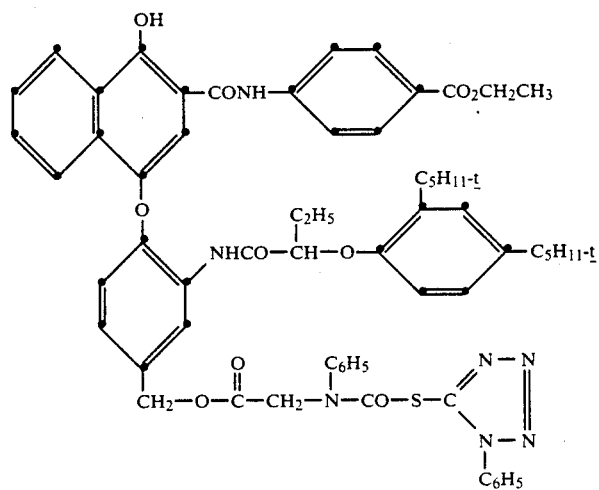
Coupler 18

TABLE I-continued
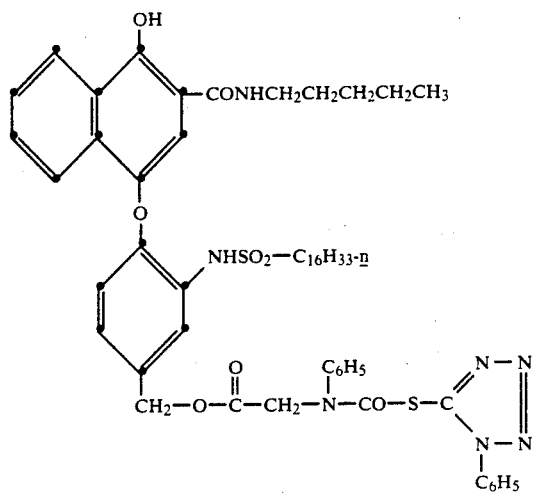
Coupler 19
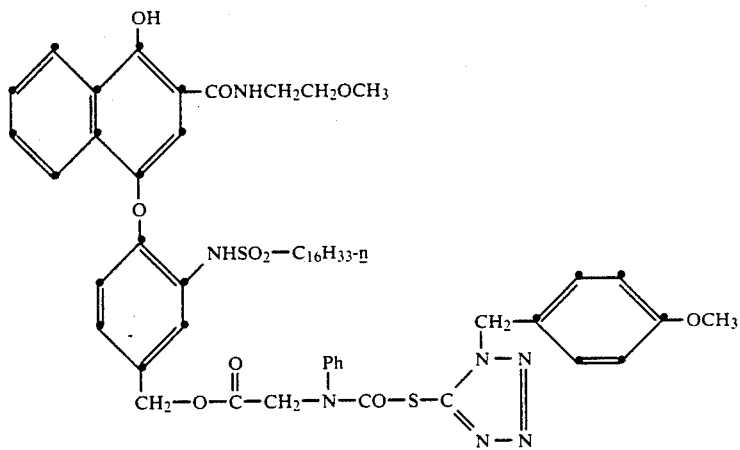
Coupler 20
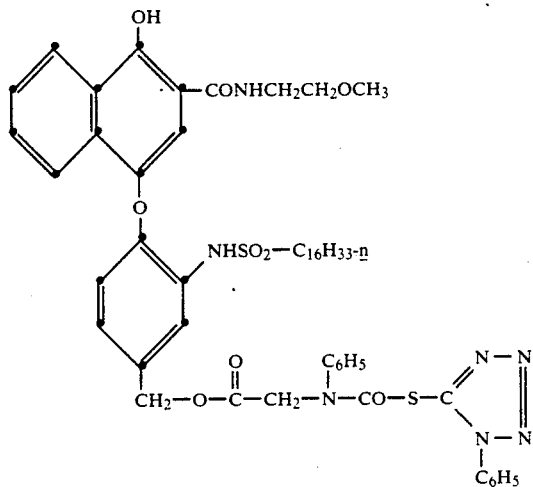
Coupler 21

TABLE I-continued
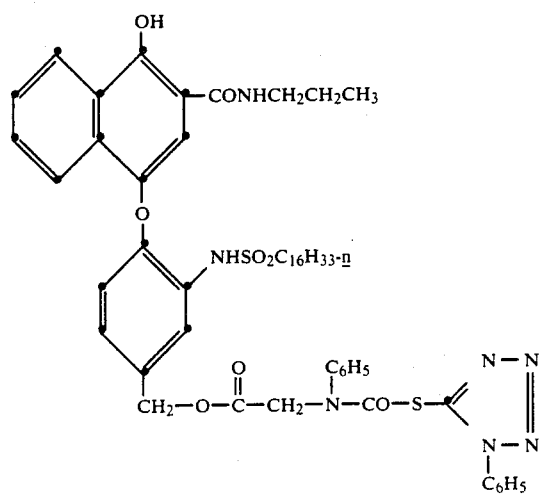
Coupler C-1 (Comparison)
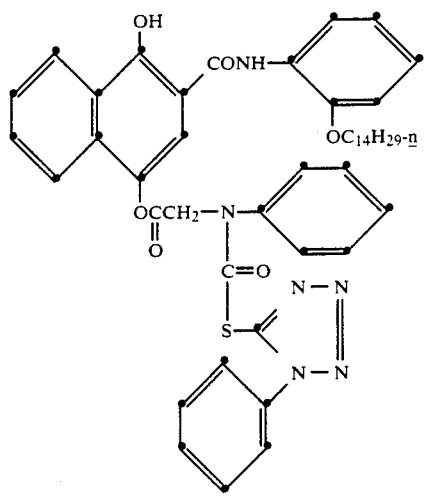
Coupler C-2 (Comparison)
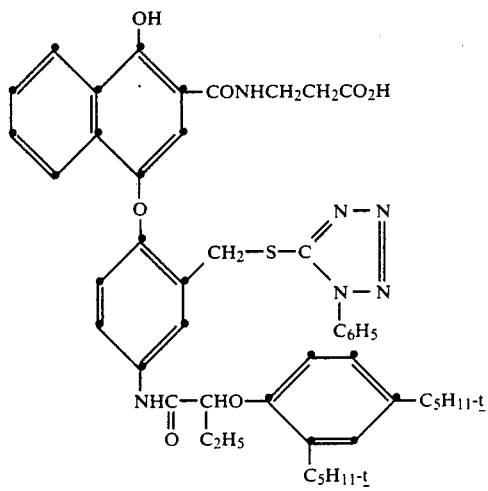
Coupler C-3 (Comparison)

TABLE I-continued

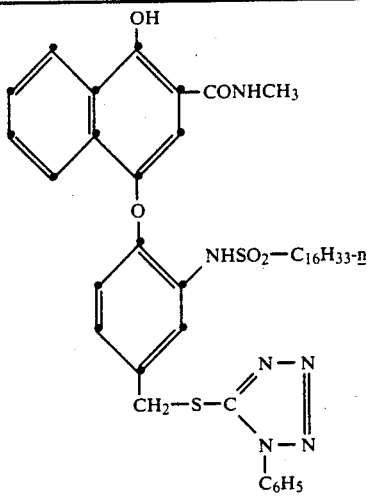

Coupler C-4 (Comparison)

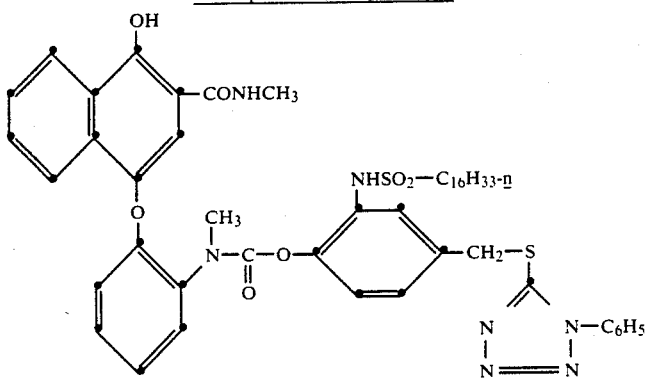

Coupler C-5 (Comparison)

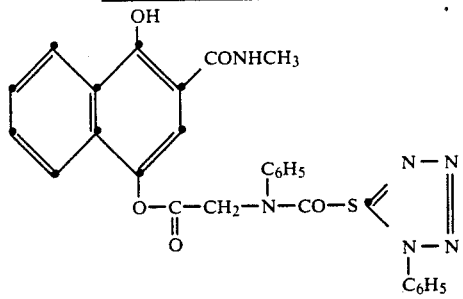

It can be seen from the interimage effects and AMT values in Table I that the use in photographic silver halide elements of couplers of the invention, which contain the described combination of groups, leads to improve sharpness and interimage effects compared to closely related compounds that do not contain such a combination of groups.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and at least one compound (A) represented by the formula SOL-CAR-LINK-PUG wherein SOL is a water solubilizing group, CAR is a carrier moiety that, upon reaction with oxidized developing agent, is capable of releasing LINK-PUG and capable of forming a compound that is washed out of the photographic element during photographic processing; LINK-PUG is in turn capable of releasing a photographically useful group (PUG) during photographic processing; and, LINK-PUG is represented by the formula:

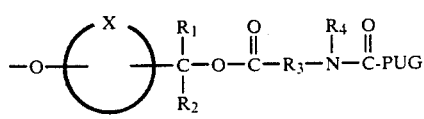

wherein

X represents the atoms necessary to complete an unsubstituted or substituted arylene or heterocyclic group;

$R_1$ and $R_2$ individually are hydrogen, alkyl, aryl or $R_1$ and $R_2$ together complete a 5- or 6-member ring;

$R_3$ is a divalent group that enables formation of a 5-, 6-, or 7-member ring upon processing of the photographic element;

$R_4$ is hydrogen, unsubstituted or substituted alkyl, or unsubstituted or substituted aryl or represents the atoms completing a ring with $R_3$; and, PUG is a releasable photographically useful group.

2. A photographic element as in claim 1 wherein CAR is a coupler moiety.

3. A photographic element as in claim 1 wherein CAR is a cyan, magenta or yellow dye-forming coupler moiety.

4. A photographic element as in claim 1 wherein LINK-PUG is represented by the formula:

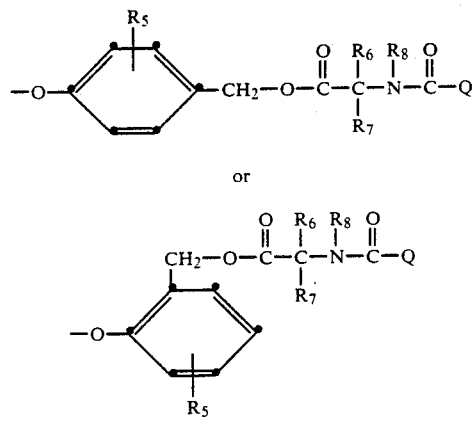

or wherein
$R_5$ is hydrogen or an substituent group;
$R_6$ and $R_7$ individually are hydrogen, alkyl or aryl;
$R_8$ is alkyl, cycloalkyl, heterocyclic or aryl; and
Q is a releasable development inhibitor group.

5. A photographic element as in claim 1 wherein the compound (A) is represented by the formula:

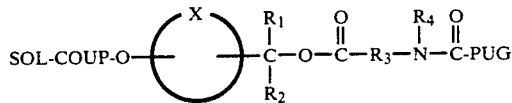

wherein
SOL is a water-solubilizing group;
COUP is a dye-forming coupler having the remainder of the molecule substituted in the coupling position;
X represents the atoms necessary to complete an arylene or heterocyclic group;
$R_1$ and $R_2$ individually are hydrogen, alkyl, aryl or $R_1$ and $R_2$ together complete a 5- or 6-member ring;
$R_3$ is a divalent group that enables formation of a 5-, 6- or 7-member ring upon processing the photographic element;
$R_4$ is hydrogen, unsubstituted or substituted alkyl or unsubstituted or substituted aryl or represents the atoms completing a ring with $R_3$;
$R_5$ is hydrogen or a substituent; and,
PUG is a releasable photographically useful group.

6. A photographic element as in claim 1 wherein LINK-PUG is represented by the formula:

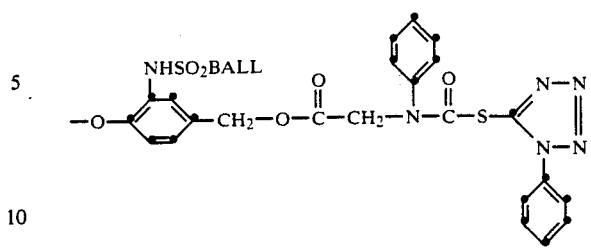

wherein BALL is a ballast group.

7. A photographic element as in claim 1 wherein SOL is a p-carboxyphenyl group.

8. A photographic element as in claim 1 wherein the compound (A) is:

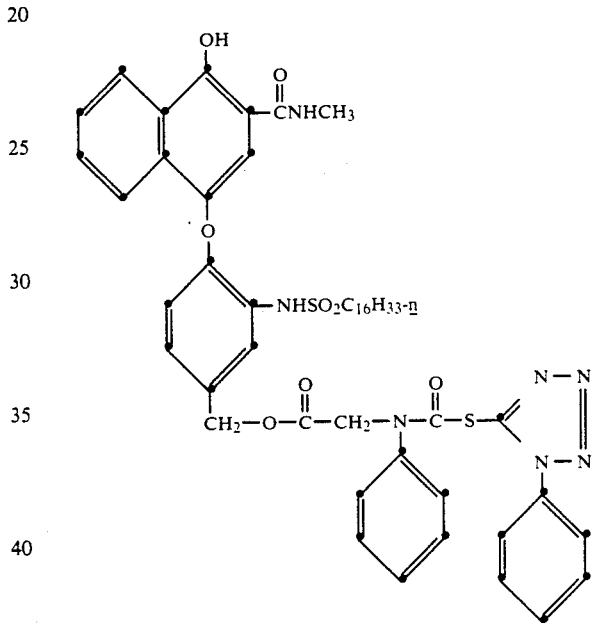

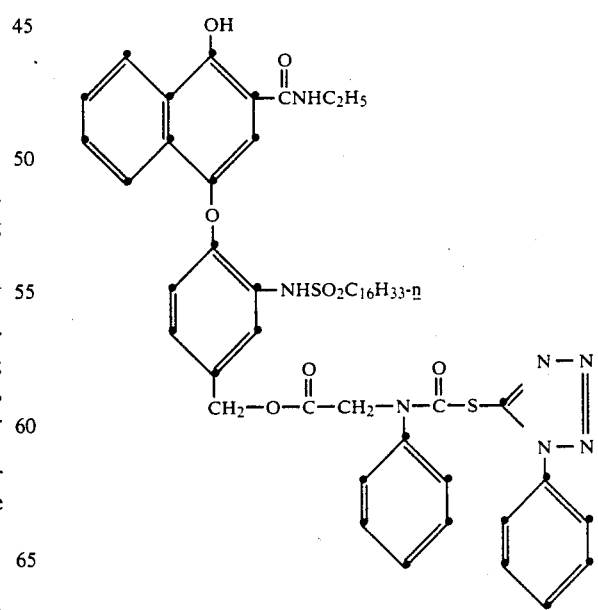

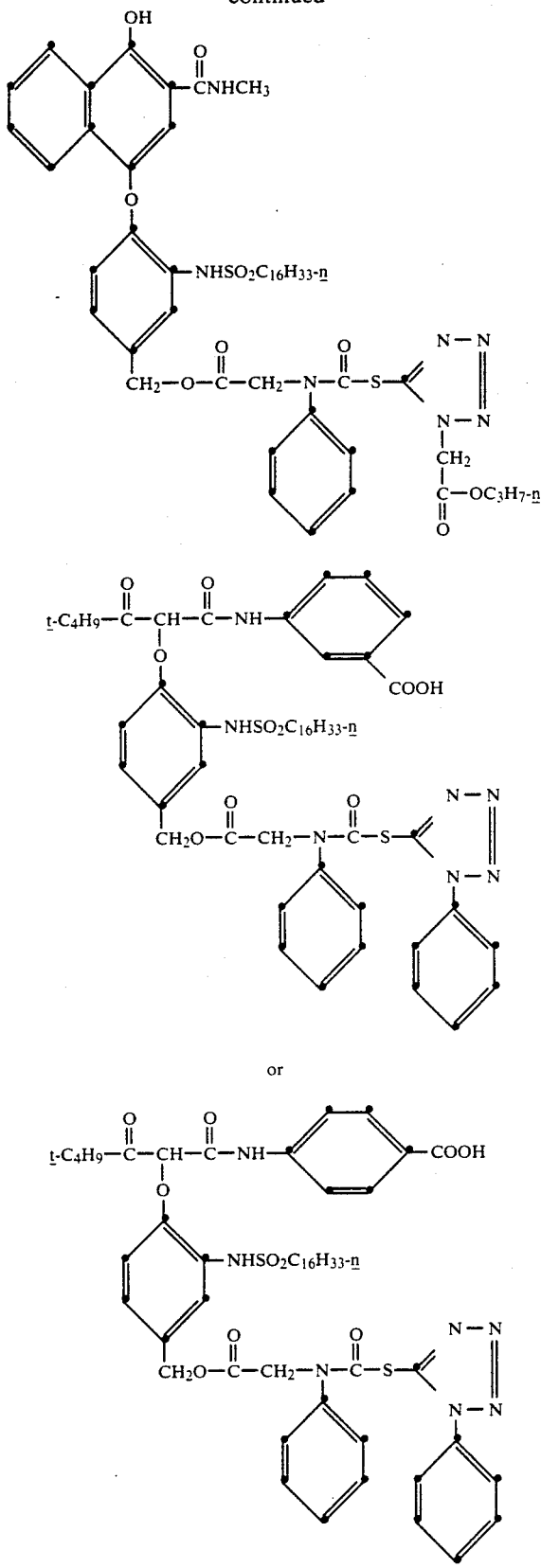

9. A photographic element as in claim 1 wherein the photographically useful group is a releasable development inhibitor, developing agent, development accelerator, bleach inhibitor, bleach accelerator, dye, dye-precursor, stabilizer, coupler, nucleator, fixing agent, image toner, hardener, antifoggant, or ultraviolet absorber.

10. A process of forming a photographic image which comprises developing an exposed photographic silver halide emulsion layer with a color developing agent in the presence of a compound (A) as defined in claim 1.

11. A process of forming a photographic image as in claim 10 wherein the compound (A) is a coupler as defined in claim 5.

12. A process as in claim 10 wherein the compound (A) is:

-continued
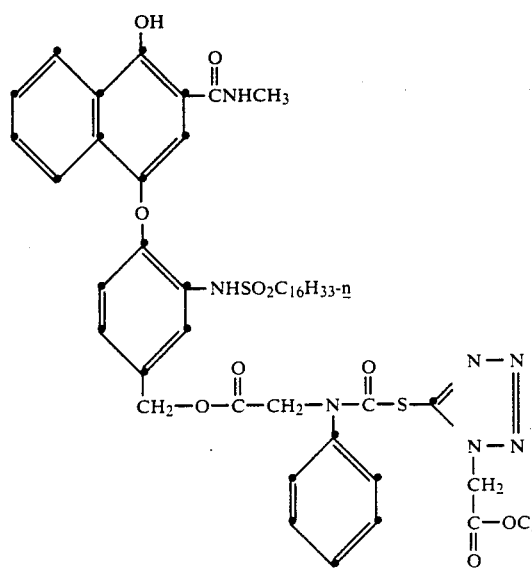
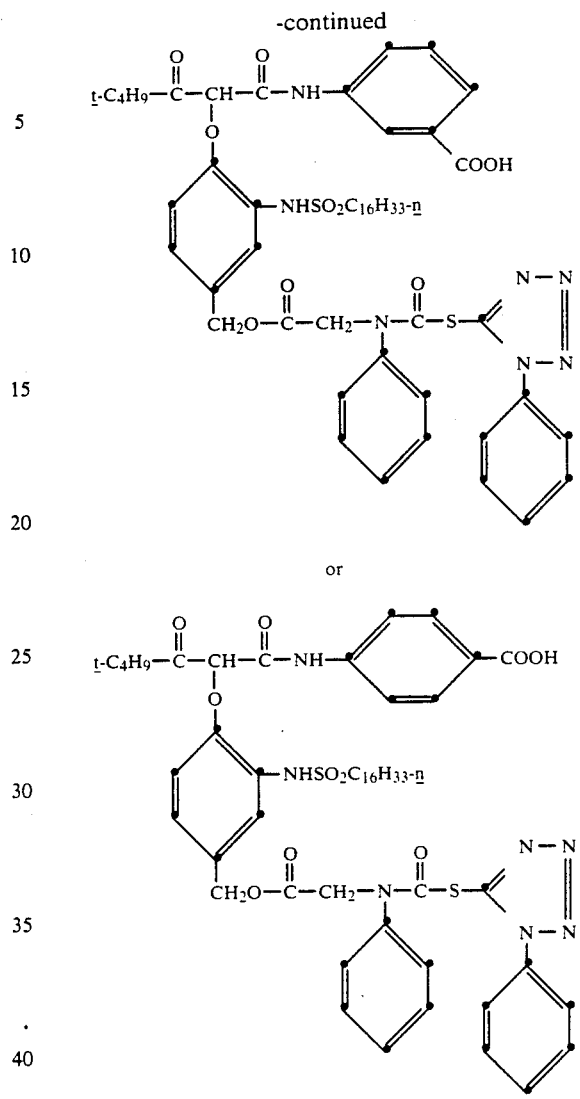
or
* * * * *